United States Patent
Tatsumi et al.

(10) Patent No.: US 6,809,091 B1
(45) Date of Patent: Oct. 26, 2004

(54) SUBSTANCES CAPABLE OF INDUCING APOPTOSIS

(75) Inventors: Yoko Tatsumi, Otsu (JP); Hiroaki Sagawa, Otsu (JP); Hiromu Ohnogi, Otsu (JP); Eiji Kobayashi, Otsu (JP); Hua-Kang Wu, Otsu (JP); Nobuto Koyama, Otsu (JP); Katsushige Ikai, Otsu (JP); Ikunoshin Kato, Otsu (JP)

(73) Assignee: Takara Bio Inc., Kyoto (JP)

( * ) Notice: Subject to any disclaimer, the term of this patent is extended or adjusted under 35 U.S.C. 154(b) by 0 days.

(21) Appl. No.: 09/582,554
(22) PCT Filed: Jan. 14, 1999
(86) PCT No.: PCT/JP99/00109
§ 371 (c)(1),
(2), (4) Date: Jun. 28, 2000
(87) PCT Pub. No.: WO99/36383
PCT Pub. Date: Jul. 22, 1999

(30) Foreign Application Priority Data

Jan. 19, 1998 (JP) .......................................... 10-020112
Mar. 31, 1998 (JP) .......................................... 10-101797
Sep. 28, 1998 (JP) .......................................... 10-288701

(51) Int. Cl.⁷ ...................... A61K 31/555; A61K 31/41; A61K 31/095; C07D 237/00; C07D 307/00
(52) U.S. Cl. ...................... 514/187; 514/186; 514/361; 514/706; 536/1.11; 544/224; 546/85; 546/136; 546/149; 549/450
(58) Field of Search .............................. 514/186, 187, 514/361, 706; 536/1.11, 1.1; 544/224; 546/85, 136, 149, 430

(56) References Cited

U.S. PATENT DOCUMENTS

| 5,015,296 A | * | 5/1991 | Dobler et al. ................. | 127/42 |
| 5,792,868 A | * | 8/1998 | Izawa et al. ................. | 544/276 |
| 5,984,882 A | * | 11/1999 | Rosenschein et al. .......... | 601/2 |
| 6,184,381 B1 | * | 2/2001 | Ikariya et al. .............. | 546/136 |

FOREIGN PATENT DOCUMENTS

| GB | 2125406 | 3/1984 |
| WO | WO 97/21443 | 6/1997 |
| WO | WO97/33593 | 9/1997 |
| WO | WO98/13328 | 4/1998 |
| WO | WO98/41196 | 9/1998 |
| WO | WO98/43623 | 10/1998 |
| WO | WO98/43624 | 10/1998 |

OTHER PUBLICATIONS

EP Search Report, Apr. 2003.

Weenen, Hugo; van der Ven, Jos G.M.; van der Linde, Leendert M.; van Duynhoven, John; Groenewegen, Anneke; "C4, C5, and C6–Deoxyglycosones: Structures and Reactivity", Spec. Publ.—R. Soc. Chem. 1998, 223 (Maillard Reaction in Foods and Medicine), pp. 57–64.

* cited by examiner

Primary Examiner—Elli Peselev
(74) Attorney, Agent, or Firm—MacCord Mason PLLC

(57) ABSTRACT

A method for the manufacture of a substance having an apoptosis-inducing ability characterized in including a step of subjecting at least one compound selected from the following (a), (b), (c) and (d) [excluding uronic acid and/or uronic acid derivatives; and compounds which contain uronic acid and/or uronic acid derivatives] to a heating treatment:

(a) pentose;
(b) pentose derivatives;
(c) compounds containing pentose;
(d) compounds containing pentose derivatives.

3 Claims, 14 Drawing Sheets

SUBSTANCES CAPABLE OF INDUCING APOPTOSIS

TECHNICAL FIELD

The present invention relates to a substance having an apoptosis-inducing ability useful in the field of pharmaceutical agents, foods and beverages, a method for the manufacture thereof, and pharmaceutical agents, foods and beverages containing said substance having an apoptosis-inducing ability.

PRIOR ART

In recent years, a mode of apoptosis has been drawing the attention concerning the death of cell tissues. Unlike necrosis which is a pathological cell death, apoptosis is a death which is integrated from the first in gene of the cell itself. Thus, a programmed death gene protein is biosynthesized by activating gene which programs the apoptosis where some external or internal cause acts as a trigger, or in other case, a programmed death protein which exists within a cell as non-activated type is activated. It is believed that the cell itself is degraded by the produced programmed death protein of activated type whereby death of the cell is resulted. If such apoptosis can be expressed in desired tissues or cells, it will be now possible to exclude the unnecessary or harmful cells from living body in their natural form and that will be significantly meaningful.

PROBLEMS TO BE SOLVED BY THE INVENTION

An object of the present invention is to offer a substance having an apoptosis-inducing ability useful in the field of pharmaceutical agents, foods and beverages, to offer a method for the manufacture thereof, and furthermore to offer pharmaceutical agents, foods and beverages containing said substance having an apoptosis-inducing ability as an effective component:

MEANS TO SOLVE THE PROBLEMS

The present inventors have carried out an intensive investigation for achieving the above-mentioned objects, found that a heat-treated product obtained by heating at least one compound selected from (a) pentose, (b) pentose derivatives such as deoxyribose, (c) compounds containing pentose such as ribonucleoside, ribonucleotide and ribonucleic acid, and (d) compounds containing pentose derivative such as deoxyribonucleoside, deoxyribonucleotide and deoxyribonucleic acid has a strong apoptosis-inducing action to cancer cells, succeeded in isolating a substance having an apoptosis-inducing ability which is an active component of said heat-treated product and accomplished the present invention.

Summary of the present invention is as follows. Thus, the first feature of the present invention relates to a method for the manufacture of a substance having an apoptosis-inducing ability characterized in including a step of subjecting at least one compound selected from the following (a), (b), (c) and (d) [excluding uronic acid and/or uronic acid derivatives; and compounds which contain uronic acid and/or uronic acid derivatives] to a heating treatment:

(a) pentose;
(b) pentose derivatives;
(c) compounds containing pentose;
(d) compounds containing pentose derivatives.

As an embodiment of the first feature of the present invention, ribose or xylose is exemplified as pentose although the present invention is not limited thereto. Examples of the pentose derivatives are deoxypentose such as deoxyribose and pentose derivatives where a group capable of having a negative charge such as phosphoric acid group or sulfuric acid group is bonded at 5-position. Examples of the compounds containing pentose are ribonucleoside, ribonucleotide, ribonucleic acid and pentose where a group of capable of having a negative charge such as phosphoric acid group or sulfuric acid group is bonded at 5-position. Examples of the compounds containing pentose derivatives are deoxyribonucleoside, deoxyribonucleotide and deoxyribonucleic acid. Examples of the substance having an apoptosis-inducing ability are the compounds selected from 4,5-dihydroxy-2-pentenal, 4-hydroxy-2-cyclopenten-1-one, 4-(9-adeninyl)-2-cyclopenten-1-one, 4-(9-guaninyl)-2-cyclopenten-1-one, 1,5-epoxy-1-hydroxy-3-penten-2-one and 4,5-dihydroxy-2-cyclopenten-1-one.

The second feature of the present invention relates to an apoptosis-inducing compound selected from 4-(9-adeninyl)-2-cyclopenten-1-one, 4-(9-guaninyl)-2-cyclopenten-1-one, 1,5-epoxy-1-hydroxy-3-penten-2-one, 2-(3,4-dihydroxy-1-butenyl)-4-(2-formylvinyl)-1,3-dioxolane and the compound represented by the following formula [I].

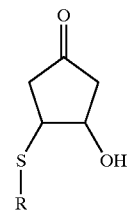

[I]

(In the formula, R is a residual group after removal of an SH group from a compound containing an SH group.)

Examples of the compound containing an SH group in the embodiment of the second feature of the present invention are cysteine and glutathione although the present invention is not limited thereto.

The third feature of the present invention relates to a pharmaceutical agent for therapy or prevention of a disease having a sensitivity to a compound selected from 4,5-dihydroxy-2-pentenal, 4-hydroxy-2-cyclopenten-1-one, 4-(9-adeninyl)-2-cyclopenten-1-one, 4-(9-guaninyl)-2-cyclopenten-1-one, 2-(3,4-dihydroxy-1-butenyl)-4-(2-formylvinyl)-1,3-dioxolane, 1,5-epoxy-1-hydroxy-3-penten-2-one and a compound represented by the formula [I], characterized in that, said pharmaceutical agent contains a compound selected from 4,5-dihydroxy-2-pentenal, 4-hydroxy-2-cyclopenten-1-one, 4-(9-adeninyl)-2-cyclopenten-1-one, 4-(9-guaninyl)-2-cyclopenten-1-one, 2-(3,4-dihydroxy-1-butenyl)-4-(2-formylvinyl)-1,3-dioxolane, 1,5-epoxy-1-hydroxy-3-penten-2-one and a compound represented by the formula [I] as an effective component.

Examples of the pharmaceutical agent in the embodiment of the third feature of the present invention are anticancer agent, apoptosis inducer, antirheumatic agent, inducer for production of human insulin-like growth factor, suppressor of the active oxygen production and inducer of the heat shock protein although the present invention is not limited thereto.

The fourth feature of the present invention relates to food or beverage where a substance having an apoptosis-inducing ability obtained by subjecting at least one compound selected from the following (a), (b), (c) and (d) [excluding uronic acid and/or uronic acid derivatives; and compounds which contain uronic acid and/or uronic acid derivatives] to a heating treatment and/or a partially purified product thereof are/is contained therein, diluted therewith and/or added thereto:

(a) pentose;

(b) pentose derivatives;

(c) compounds containing pentose;

(d) compounds containing pentose derivatives.

Examples of the food or beverage in the embodiment of the fourth feature of the present invention are carcinostatic, apoptosis-inducing, antirheumatic, human insulin-like growth factor production inducing, active oxygen production suppressing and heat shock protein inducing food or beverage although the present invention is not limited thereto.

EMBODIMENTS OF THE INVENTION

Figure 1:
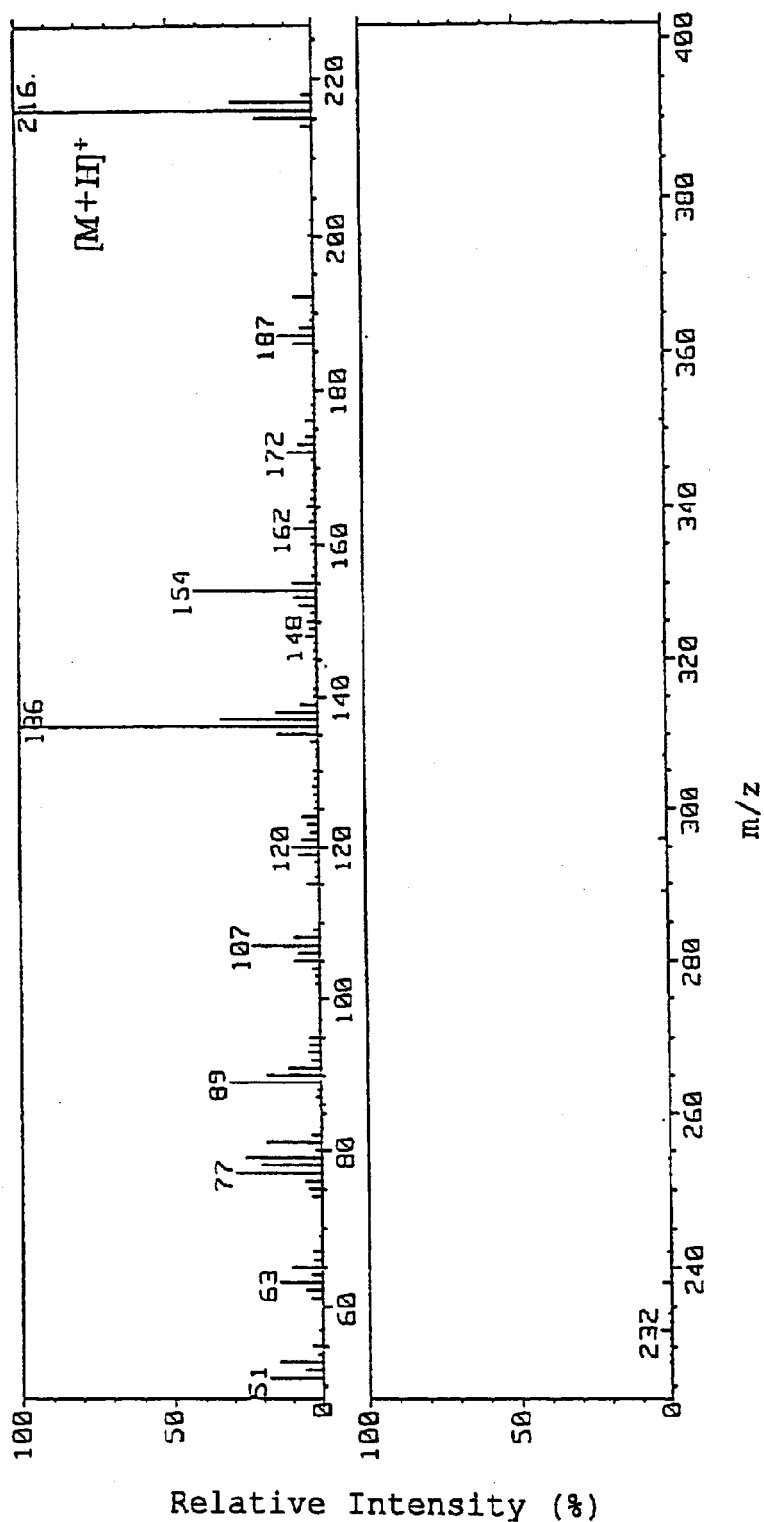
FIG. 1 shows a mass spectrum of 4-(9-adeninyl)-2-cyclopenten-1-one.

The present invention will now be specifically illustrated as hereinafter.

Pentose is a general name for saccharides having five carbons and arabinose, xylose, ribose, lyxose, etc. are present in nature as aldopentose while ribulose and xylulose are present in nature as ketopentose.

Examples of the pentose derivative are deoxypentose and pentitol and, for the former, deoxyribose while, for the latter, ribitol, arabitol and xylitol are present in nature. In addition, aminosaccharide, aldonic acid, aldaric acid, etc. having five carbons are pentose derivatives as well and they can be prepared by a synthetic method, etc.

Examples of the compound containing pentose are low-molecular compounds such as pentose phosphate, ribonucleoside and ribonucleotide and high-molecular compounds such as ribonucleic acid, arabinan and xylan. Esters, ethers, glycosides, etc. of pentose and salts thereof are the compounds containing pentose as well and they are prepared by a synthetic method, etc.

Examples of the compound containing pentose derivative are deoxypentose phosphate, deoxyribonucleoside, deoxyribonucleotide and deoxyribonucleic acid containing deoxypentose and riboflavin and ribitolteichoic acid containing pentitol. Esters, ethers, amides, glycosides, etc. of pentose derivatives and salts thereof are the compounds containing pentose derivatives as well and they are prepared by a synthetic method, etc.

Ribonucleic acid, ribonucleotide, ribonucleoside, deoxyribonucleic acid, deoxyribonucleotide and deoxyribonucleoside act as coenzymes or play a role of conservation and expression of genetic information and are quite important substances for living organisms. Ribose-5-phosphate, ribulose-5-phosphate and xylulose-5-phosphate are found in wide ranges of organisms as metabolic intermediates of pentose phosphate cycle. Plant gummy substances, mucilage, hemicellulose and bacterial polysaccharide contain arabinose and xylose and lyxoflavine in human heart muscle and a certain type of antibiotics are derivatives of lyxose.

Pentose where a group capable of having a negative charge is bonded at 5-position and a compound containing pentose where a group capable of having a negative charge is bonded at 5-position are also included in the compound containing pentose used in the present invention. In the present invention, a group which is capable of having a negative charge may be any group so far as it has a negative charge in an aqueous solution under at least one condition of pH 1–13 and 0° C.–200° C. and its examples are phosphoric acid group and sulfuric acid group. Further, in the present specification, salts, esters and acid anhydrides thereof are included in a group capable of having a negative charge. However, although a carboxyl group is a group which is able to have a negative charge, aldopentose having a carboxyl group at 5-position is uronic acid and, therefore, it is excluded from the compound containing pentose used in the present invention.

There is no particular limitation for pentose where a group capable of having a negative charge is bonded at 5-position which can be used in the present invention and all substances having an apoptosis-inducing ability, for example substances which produce 4,5-dihydroxy-2-cyclopenten-1-one, are included in the compound containing pentose of the present invention. Thus, when 4,5-dihydroxy-2-cyclopenten-1-one for example is produced by a heating treatment, there is no limitation for the type of the pentose and for the type of the group capable of having a negative charge. Examples of the pentose where a group capable of having a negative charge is bonded at 5-position are ribose-5-phosphate and ribose-5-sulfate.

There is no particular limitation for the compound containing pentose where a group capable of having a negative charge is bonded at 5-position and its examples are ribonucleic acid, ribonucleotide and ribonucleoside as well as degraded products thereof, derivatives of the degraded products and salts of the degraded products which are the products prepared by chemical, enzymatic or physical treatment thereof can be used.

In the present invention, there is no limitation at all for the type of the above pentose, pentose derivative, compound containing pentose and compound containing pentose derivative so far as a substance having an apoptosis-inducing ability is produced by a heating treatment. Pentose, pentose derivative, compound containing pentose and compound containing pentose derivative are obtained by extraction of animals, plants or microorganisms, manufactured by a fermentation method, synthesized by a chemical means, etc. and a product by any of the manufacturing means can be used in the present invention so far as a substance which has an apoptosis-inducing ability is formed by a heating treatment.

In the present invention, a substance which contains pentose, pentose derivative, compound containing pentose and/or compound containing pentose derivative may be used as well. Tissues of animals and plants and cells of animals, plants and microorganisms contain various types of pentose, pentose derivative, compound containing pentose and compound containing pentose derivative and, therefore, they may be used in the present invention as they are. Incidentally, in the present invention, compounds containing uronic acid and/or uronic acid derivative are excluded from the compound containing pentose and/or pentose derivative. Uronic acid derivative means uronic acid lactone, uronic acid ester, uronic acid amide, uronic acid salt, etc.

In the present invention, there is no particular limitation for the method of the heating treatment in the manufacture of the substance having an apoptosis-inducing ability so far as it is under the condition whereby a heat-treated product having an apoptosis-inducing ability is obtained and, for example, at least one compound selected from the above-mentioned (a) to (d) (excluding uronic acid and/or uronic acid derivative and a compound containing uronic acid and/or uronic acid derivative) is heated at 30–400° C. for from a few seconds to a few days or, preferably, at 50–200° C. for from a few seconds to 24 hours whereupon a heat-treated product having an apoptosis-inducing ability can be obtained. In the heat-treated product, two or more substances having an apopotosis-inducing ability are produced and, depending upon the object, the heat treating conditions such as pH, time, temperature and concentration of materials may be modified whereupon a heat-treated product having an apoptosis-inducing ability containing a desired substance can be prepared.

For example, when ribose or ribose-5-phosphate are used, a heat-treated product containing 4,5-dihydroxy-2-cyclopenten-1-one can be obtained by heating, for example, at 80–150° C. for a few minutes to a few days.

As hereunder, the heat-treated product of the compound selected from the above (a) to (d) having an apoptosis-inducing ability will be just referred to as a heat-treated product of the present invention.

There is no particular limitation for the concentration of the material upon heating provided that the concentration is within such a range that the substance having an apoptosis-inducing ability can be obtained by the heating treatment. Thus, the concentration may be decided by taking workability, yield, etc. into consideration. The heating treatment in the present invention may be either wet heating or dry heating. In the case of a wet heating, any of wet heating methods such as heating with steam, heating with steam under high pressure, heating under high pressure, etc. may be used while, in the case of a dry heating, any of dry heating methods such as a direct heating using dry and hot air and an indirect heating from a heat source through a partition may be used. Examples of the direct heating are a dry heating by an air stream and a dry heating by means of spraying while those of the indirect heating are a dry heating by means of a drum, etc. In addition, the material for the substance having an apoptosis-inducing ability of the present invention may be treated by any of common heating methods such as boiling, toasting, roasting, decocting, steaming, frizzling, frying, and the like.

The substance having an apoptosis-inducing ability of the present invention can be purified using an apoptosis-inducing action as an index. As for the purifying means, conventionally known purifying means such as chemical method and physical method can be used.

For example, when ribose is used and its 2M aqueous solution is heated at 121° C. for 14 hours, 4,5-dihydroxy-2-cyclopenten-1-one is produced in the heat-treated product. The 4,5-dihydroxy-2-cyclopenten-1-one in the heat-treated product is extracted with a solvent and the extract is concentrated. The concentrate is separated by a silica gel column chromatography, the eluted 4,5-dihydroxy-2-cyclopenten-1-one fraction is concentrated, then 4,5-dihydroxy-2-cyclopenten-1-one is extracted from the concentrate with chloroform, and the concentrated extract is subjected to a normal phase column chromatography whereupon 4,5-dihydroxy-2-cyclopenten-1-one in the heat-treated product of the present invention is isolated.

When the above heat-treated product of ribose is subjected to a treatment with a column of ion exchange resin or, preferably, a column of anionic ion exchange resin and the non-adsorbing fractions are collected whereupon 4,5-dihydroxy-2-cyclopenten-1-one is purified. Alternatively, the above heat-treated product of ribose is treated with a column of activated charcoal, non-adsorbing fractions are removed and the column is washed and eluted with a hydrophilic organic solvent such as an aqueous solution of ethanol, preferably a 40% or higher aqueous solution of ethanol, to give pure 4,5-dihydroxy-2-cyclopenten-1-one. When those methods are combined, pure 4,5-dihydroxy-2-cyclopenten-1-one of higher purity can be obtained.

By the use of the same purifying means, it is possible to obtain a compound selected from 4,5-dihydroxy-2-pentenal, 4-hydroxy-2-cyclopenten-1-one, 4-(9-adeninyl)-2-cyclopenten-1-one, 4-(9-guaninyl)-2-cyclopenten-1-one and 1,5-epoxy-1-hydroxy-3-penten-2-one from the heat-treated product of the present invention.

Incidentally, the pure product and the partially pure product which are purified by such purifying means are also included in the substance having an apoptosis-inducing ability of the present invention.

The present inventors have found that trans-4,5-dihydroxy-2-cyclopentenal mentioned in *Biochemistry*, 35, 659–665 (1996) and analogs thereof are contained in the heat-treated product of the present invention and have found that those compounds show an anticancer action, an apoptosis-inducing action, etc.

The present inventors have also succeeded in isolating 4-hydroxy-2-cyclopenten-1-one, 4-(9-adeninyl)-2-cyclopenten-1-one, 4-(9-guaninyl)-2-cyclopenten-1-one, 1,5-epoxy-1-hydroxy-3-penten-2-one and 4,5-dihydroxy-2-cyclopenten-1-one from the heat-treated product of the present invention. They have further found that 2-(trans-3,4-dihydroxy-1-butenyl)-4-(trans-2-formylvinyl)-1,3-dioxolane is produced from 4,5-dihydroxy-2-pentenal and succeeded in isolating it. They have furthermore found that 4-hydroxy-2-cyclopenten-1-one reacts with an SH-containing compound to give a compound represented by the formula [I] and succeeded in isolating it. They have still further found that those compounds have physiological activities such as an activity for suppressing the growth of cancer cells and an apoptosis-inducing activity.

Accordingly, when a compound selected from 4,5-dihydroxy-2-pentenal, 4-hydroxy-2-cyclopenten-1-one, 4-(9-adeninyl)-2-cyclopenten-1-one, 4-(9-guaninyl)-2-cyclopenten-1-one, 2-(3,4-dihydroxy-1-butenyl)-4-(2-formylvinyl)-1,3-dioxolane, 1,5-epoxy-1-hydroxy-3-penten-2-one and a compound represented by the formula [I] (hereinafter, referred to the compound of the present invention) is used as an effective component, it is now possible to offer a pharmaceutical agent for the therapy or the prevention of a diseases which shows a sensitivity to the compound of the present invention such as cancerous disease, disease requiring the apoptosis induction, disease requiring the suppression of the active oxygen production, disease requiring the induction of production of human insulin-like growth factor, disease requiring the induction of heat shock protein production, etc.

When a compound which is selected from the heat-treated product of the present invention or the compound of the present invention is used as an effective component and is made into a pharmaceutical preparation by compounding with known pharmaceutical carriers, it is now possible to prepare an apoptosis inducer. Generally, a compound which is selected from the heat-treated product of the present invention or the compound of the present invention is compounded with a pharmaceutically acceptable liquid or solid carrier and, if necessary, solvent, dispersing agent, emulsifier, buffer, stabilizer, filler, binder, disintegrating agent, lubricant, etc. are added thereto to give an apoptosis inducer which may be in solid such as tablets, granules, diluted powders, powders, capsules, etc. or in liquid such as solutions, suspensions, emulsions, etc. Further, this may be in a dry preparation which can be made into liquid by adding an appropriate carrier before use.

The apoptosis inducer of the present invention can be administered either orally or parenterally by, for example, injection or intravenous drip infusion.

The pharmaceutical carrier may be selected depending upon the above-mentioned mode of the administration and form of the preparation. In the case of oral preparations, starch, lactose, sugar, mannitol, carboxymethyl cellulose, corn starch, inorganic salts, etc. may be used. In the manufacture of oral preparations, binders, disintegrating agents, surface-active agents, lubricants, fluidity promoters, taste-correctives, coloring agents, flavors, etc. may be further compounded therewith.

On the other hand, in the case of parenteral preparations, they may be prepared by common methods where a compound which is selected from the heat-treated product of the present invention or the compound of the present invention which is an effective component of the present invention is dissolved or suspended in a diluent such as distilled water for injection, physiological saline solution, aqueous solution of glucose, vegetable oil for injection, sesame oil, peanut oil, soybean oil, corn oil, propylene glycol, polyethylene glycol, etc. followed, if necessary, by adding bactericides, stabilizers, isotonic agents, analgesics, etc. thereto.

The apoptosis inducer which contains a compound which is selected from the heat-treated product of the present invention or the compound of the present invention is administered by an appropriate route depending upon the form of the preparation. There is no particular limitation for the method of administration as well and it may be administered by means of oral use, external use and injection. Injection preparations are administered, for example, intravenously, intramuscularly, subcutaneously, intracutaneously, etc. while preparations for external use include suppositories, etc.

Dose as an apoptosis inducer which contains the heat-treated product of the present invention as an effective component is appropriately decided by its form of preparation, method of administration, purpose of use and age, body weight and symptom of the patient to be treated and it is not constant but, usually, the amount of the effective component contained in the preparation is from 1 to 1000 mg, preferably 10 to 200 mg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

Dose as an apoptosis inducer which contains the compound selected from the compound of the present invention as an effective component is appropriately decided by its form of preparation, method of administration, purpose of use and age, body weight and symptom of the patient to be treated and it is not constant but, usually, the amount of the effective component contained in the preparation is from 0.01 to 50 mg, preferably 0.1 to 10 mg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

The heat-treated product of the present invention or the compound of the present invention has an apoptosis-inducing action to cancer cells, a cell growth suppressing action and a topoisomerase II inhibiting action. An anticancer agent can be manufactured where a heat-treated product of the present invention or the compound of the present invention is used as an effective component. Thus, when a heat-treated product of the present invention or the compound of the present invention is used as an effective component and is made into a preparation by combining with the known pharmaceutical carrier, an anticancer agent can be manufactured. Manufacture of the anticancer agent can be carried out by a method similar to that mentioned already.

The anticancer agent can be administered either orally or parenterally by, for example, injection or intravenous drip infusion.

The pharmaceutical carrier may be selected depending upon the above-mentioned mode of the administration and form of the preparation, and may be used by the same manner as in the case of the above-mentioned apoptosis inducer.

The anticancer agent is administered by an appropriate route depending upon the form of the preparation. There is no particular limitation for the method of administration as well and it may be administered by means of oral use, external use and injection. Injection preparations are administered, for example, intravenously, intramuscularly, subcutaneously, intracutaneously, etc. while preparations for external use include suppositories, etc.

Dose as an anticancer agent which contains the heat-treated product of the present invention as an effective component is appropriately decided by its form of preparation, method of administration, purpose of use and age, body weight and symptom of the patient to be treated and it is not constant but, usually, the amount of the heat-treated product of the present invention contained in the preparation is from 1 to 1000 mg, preferably 10 to 200 mg per day (for adults) Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

Dose as an anticancer agent which contains the compound selected from the compound of the present invention as an effective component is appropriately decided by its form of preparation, method of administration, purpose of use and age, body weight and symptom of the patient to be treated and it is not constant but, usually, the amount of the effective component contained in the preparation is from 0.01 to 50 mg, preferably 0.1 to 10 mg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

Rheumatism is an autoimmune disease where hindrance takes place in perisoteal cells and cartilage cells. The heat-treated product of the present invention or the compound of the present invention has an apoptosis-inducing action to synovial cells. Accordingly, an antirheumatic agent can be manufactured where a heat-treated product of the present invention or the compound of the present invention is used as an effective component. Thus, when a heat-treated product of the present invention or the compound of the present invention is used as an effective component and is made into a preparation by combining with the known pharmaceutical carrier, an antirheumatic agent can be manufactured. Manufacture of the antirheumatic agent can be carried out by a method similar to that mentioned already.

The antirheumatic agent can be administered either orally or parenterally by, for example, injection or intravenous drip infusion.

The pharmaceutical carrier may be selected depending upon the above-mentioned mode of the administration and form of the preparation, and may be used by the same manner as in the case of the above-mentioned apoptosis inducer.

The antirheumatic agent is administered by an appropriate route depending upon the form of the preparation. There is no particular limitation for the method of administration as well and it may be administered by means of oral use, external use and injection. Injection preparations are administered, for example, intravenously, intramuscularly, subcutaneously, intracutaneously, etc. while preparations for external use include suppositories, etc.

Dose as an antirheumatic agent which contains the heat-treated product of the present invention as an effective component is appropriately decided by its form of preparation, method of administration, purpose of use and age, body weight and symptom of the patient to be treated and it is not constant but, usually, the amount of the heat-treated product of the present invention contained in the preparation is from 1 to 1000 mg, preferably 10 to 200 mg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

Dose as an antirheumatic agent which contains the compound selected from the compound of the present invention as an effective component is appropriately decided by its form of preparation, method of administration, purpose of use and age, body weight and symptom of the patient to be treated and it is not constant but, usually, the amount of the effective component contained in the preparation is from 0.01 to 50 mg, preferably 0.1 to 10 mg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

Human insulin growth factor (hereinafter, referred to as hIGF-1) has variegated physiological actions to various cells and has been used as a therapeutic agent for diabetes mellitus of type II (non-insulin dependent) and for failure to thrive (dwarfism). A heat-treated product of the present invention or the compound of the present invention has an action of inducing the hIFG-1 production. Accordingly, a hIGF-1 production inducer can be manufactured where a heat-treated product of the present invention or the compound of the present invention is used as an effective component. Thus, when a heat-treated product of the present invention or the compound of the present invention is used as an effective component and is made into a preparation by combining with the known pharmaceutical carrier, a hIGF-1 production inducer can be manufactured. Manufacture of the hIGF-1 production inducer can be carried out by a method similar to that mentioned already. A hIGF-1 production inducer can be used as a therapeutic and preventive agent for disease requiring the induction of hIGF-1 production and for diabetes mellitus of type II and also a therapeutic agent for dwarfism.

The hIGF-1 production inducer can be administered either orally or parenterally by, for example, injection or intravenous drip infusion.

The pharmaceutical carrier may be selected depending upon the above-mentioned mode of the administration and form of the preparation, and may be used by the same manner as in the case of the above-mentioned apoptosis inducer.

The hIGF-1 production inducer is administered by an appropriate route depending upon the form of the preparation. There is no particular limitation for the method of administration as well and it may be administered by means of oral use, external use and injection. Injection preparations are administered, for example, intravenously, intramuscularly, subcutaneously, intracutaneously, etc. while preparations for external use include suppositories, etc.

Dose as a hIGF-1 production inducer which contains the heat-treated product of the present invention as an effective component is appropriately decided by its form of preparation, method of administration, purpose of use and age, body weight and symptom of the patient to be treated and it is not constant but, usually, the amount of the heat-treated product of the present invention contained in the preparation is from 1 to 1000 mg, preferably 10 to 200 mg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

Dose as a hIGF-1 production inducer which contains the compound selected from the compound of the present invention as an effective component is appropriately decided by its form of preparation, method of administration, purpose of use and age, body weight and symptom of the patient to be treated and it is not constant but, usually, the amount of the effective component contained in the preparation is from 0.01 to 50 mg, preferably 0.1 to 10 mg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

The heat-treated product of the present invention or the compound of the present invention has an action of suppressing the active oxygen production and it is possible to manufacture a suppressor of active oxygen production where the heat-treated product of the present invention or the compound of the present invention is an effective component and said suppressor can be administered by a method corresponding to the disease which requires suppression of active oxygen production.

Thus, the heat-treated product of the present invention or the compound of the present invention is useful in suppressing the active oxygen production and an antioxidant such as a suppressor of the active oxygen production containing said compound as an effective component is useful as a therapy or a prevention of diseases caused by production and/or overflow of active oxygen.

Active oxygen may be roughly classified into radical and non-radical ones. Examples of active oxygen of a radical type are hydroxy radical, hydroxyperoxy radical, peroxy radical, alkoxy radical, nitrogen dioxide, nitrogen monoxide (hereinafter, referred to as NO), thiyl radical and superoxide while examples of active oxygen of a non-radical type are singlet oxygen, hydrogen peroxide, lipid hydroperoxide, hypochlorous acid, ozone and peroxynitrous acid. All of them relate to many diseases such as various inflammatory diseases, diabetes mellitus, cancer, arteriosclerosis, nervous diseases and ischemia-reperfusion injury.

For example, NO is a main factor of endothelium-dependent relaxing factor (EDRF) [Nature, volume 327, pages 524–526 (1987)]. The present invention offers a therapeutic or preventive agent for the diseases requiring the suppression of NO production.

There is no particular limitation for the diseases which require the suppression of NO production and the examples thereof are systemic hypotension caused by toxic shock or by therapy of certain cytokine, lowering in blood pressure response, autoimmune diseases, inflammation, arthritis, rheumatic arthritis, diabetes mellitus, inflammatory intestine diseases, insufficiency of blood vessel function, etiological dilation of blood vessel, damage of tissues, cardiovascular ischemia, sensitivity to pain, cerebral ischemia, diseases caused by angiogenesis, cancer, etc. The diseases include those which are mentioned in the Japanese Laid-Open Patent Publications Hei-09/504,524; 09/505,288; 08/501,069; 08/512,318; and 06/508,849. A suppressor of the active oxygen production is useful for therapy and prevention of the diseases requiring the suppression of NO production as a suppressor of the NO production.

The suppressor of the active oxygen production can be administered either orally or parenterally by, for example, injection or intravenous drip infusion.

The pharmaceutical carrier may be selected depending upon the above-mentioned mode of the administration and form of the preparation, and may be used by the same manner as in the case of the above-mentioned apoptosis inducer.

The suppressor of the active oxygen production is administered by an appropriate route depending upon the form of the preparation. There is no particular limitation for the method of administration as well and it may be administered by means of oral use, external use and injection. Injection preparations are administered, for example, intravenously, intramuscularly, subcutaneously, intracutaneously, etc. while preparations for external use include suppositories, etc.

Dose as a suppressor of the active oxygen production which contains the heat-treated product of the present invention as an effective component is appropriately decided by its form of preparation, method of administration, purpose of use and age, body weight and symptom of the patient to be treated and it is not constant but, usually, the amount of the heat-treated product of the present invention contained in the preparation is from 1 to 1000 mg, preferably 10 to 200 mg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

Dose as a suppressor of the active oxygen production which contains the compound selected from the compound of the present invention as an effective component is appropriately decided by its form of preparation, method of administration, purpose of use and age, body weight and symptom of the patient to be treated and it is not constant but, usually, the amount of the effective component contained in the preparation is from 0.01 to 50 mg, preferably 0.1 to 10 mg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

The heat-treated product of the present invention or the compound of the present invention has an action of inducing the heat shock protein production and it is possible to manufacture an inducer of the heat shock protein where the heat-treated product of the present invention or the compound of the present invention is an effective component and said inducer can be administered by a method corresponding to the disease which requires the induction of heat shock protein.

Accordingly, the heat-treated product of the present invention or the compound of the present invention has an inducing activity of heat shock protein 70 kDa (HSP70), etc.

and has an antiviral activity to RNA virus and DNA virus such as hepatitis virus, AIDS virus, influenza virus, vesicular stomatitis virus and herpesvirus. Heat shock protein participates in cancer immunity and those compounds are effective to cancer immunity as well. Further, the compounds has biodefense activity such as anti-inflammation activity. When the heat-treated product of the present invention or the compound of the present invention is taken, viral diseases such as cold by influenza can be prevented and cured.

Incidentally, heat shock protein is a general name for the protein whose synthesis is induced when cell or individual is subjected to a sudden temperature change which is higher than normal temperature to an extent of around 5–10° C. and it widely exists in prokaryotes and high eukaryotes. Examples of known heat shock protein are HSP90, HSP70, ubiquitin and HSP26. Among them, HSP70 is a kind of molecular chaperone and is bonded to protein where folding is not completed or is incompletely done to assist the formation of stereostructure. Amino acid sequence of the heat shock protein has been well conserved during the course of evolution and HSP70 is identical with DnaK protein of *Escherichia coli*. In human being, there are about ten HSP70 genes and some of them are expressed constitutionally while other are induced by various stimulations. Besides the heat shock, synthesis of heat shock protein is induced by various chemical substances and by cellular hindrance such as oxidation.

The inducer of the heat shock protein can be administered either orally or parenterally by, for example, injection or intravenous drip infusion.

The pharmaceutical carrier may be selected depending upon the above-mentioned mode of the administration and form of the preparation, and may be used by the same manner as in the case of the above-mentioned apoptosis inducer.

The inducer of the heat shock protein is administered by an appropriate route depending upon the form of the preparation. There is no particular limitation for the method of administration as well and it may be administered by means of oral use, external use and injection. Injection preparations are administered, for example, intravenously, intramuscularly, subcutaneously, intracutaneously, etc. while preparations for external use include suppositories, etc.

Dose as an inducer of the heat shock protein which contains the heat-treated product of the present invention as an effective component is appropriately decided by its form of preparation, method of administration, purpose of use and age, body weight and symptom of the patient to be treated and it is not constant but, usually, the amount of the heat-treated product for apoptosis-inducing contained in the preparation is from 1 to 1000 mg, preferably 10 to 200 mg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

Dose as an inducer of the heat shock protein which contains the compound selected from the compound of the present invention as an effective component is appropriately decided by its form of preparation, method of administration, purpose of use and age, body weight and symptom of the patient to be treated and it is not constant but, usually, the amount of the effective component contained in the preparation is from 0.01 to 50 mg, preferably 0.1 to 10 mg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

A compound which is selected from the heat-treated product of the present invention and/or a partially purified product thereof or the compound of the present invention may be used as a material for apoptosis-inducing food/beverage, carcinostatic food/beverage, antirheumatic food/beverage, hIGF-1 production inducing food/beverage, active oxygen production suppressing food/beverage or heat shock protein inducing food/beverage.

Food or beverage where a compound which is selected from the heat-treated product of the present invention and/or a partially purified product thereof or the compound of the present invention are/is contained therein, diluted therewith and/or added thereto is sufficient if said food or beverage contains an amount that is necessary for expressing the physiological action of a compound which is selected from the heat-treated product of the present invention and/or a partially purified product thereof or the compound of the present invention.

There is no particular limitation for the method of manufacturing the food or beverage of the present invention such as apoptosis-inducing food, apoptosis-inducing beverage, carcinostatic food and carcinostatic beverage and the manufacture by a method of manufacturing food or beverage which has been used for cooking, processing and others in general may be used so far as an effective amount of the compound selected from the heat-treated product and/or partially purified product thereof or the compound of the present invention having apoptosis-inducing action, anticancer action, etc. is contained in, diluted with and/or added to the manufactured food or beverage are/is contained therein, diluted therewith and/or added thereto.

The partially purified product of the heat-treated product of the present invention is obtained by purification of the heat-treated product of the present invention where there is no limitation for it so far as it has an apoptosis-inducing ability and there is no particular limitation for it provided that it is a product obtained by a usual method in a purifying step of food and beverage materials.

For such food and beverage, there is no particular limitation for its shape so far as an effective amount of the compound selected from the heat-treated product and/or partially purified product thereof or the compound of the present invention having apoptosis-inducing action, anticancer action, etc. are/is contained therein, diluted therewith and/or added thereto and the said includes the shapes which can be orally administered such as tablets, granules, capsules, gel and sol.

When a physiologically active effective dose of the heat-treated product of the present invention and partially purified product thereof and the compound of the present invention are/is administered to mice, no acute toxicity is noted. For example, there is no case of death by a single oral administration of each 100 mg/kg of 4,5-dihydroxy-2-pentenal and 4-hydroxy-2-cyclopenten-1-one.

The pharmaceutical agent of the present invention is useful for keeping the homeostasis of living body. In addition, a method for the induction of apoptosis using the compound selected from the heat-treated product of the present invention and/or partially purified product thereof or the compound of the present invention as an effective component is useful in investigation of defense mechanism of organism, immune mechanism or the relation between cancer, viral diseases, etc. and living body, in development of apoptosis-inducing inhibitors, etc.

When the heat-treated product of the present invention and/or a partially purified product are/is contained in food or beverage, it is possible to manufacture apoptosis-inducing food or beverage, carcinostatic food or beverage, antirheumatic food or beverage, hIGF-1 production inducing food or beverage, active oxygen production suppressing food or beverage, or heat shock protein inducing food or beverage. Food or beverage containing the heat-treated product of the present invention and/or purified product thereof is a health food or beverage having an effect of prevention of carcinogenesis, an anticancer effect, an antiviral effect, etc. by taking it and is food or beverage useful for maintaining the homeostasis, particularly maintaining the health of stomach and intestine, of organism due to various physiological activities of said heat-treated product and/or purified product thereof such as apoptosis-inducing action, anticancer action, antirheumatic action, hIGF-1 production inducing action, active oxygen production suppressing action and heat shock protein inducing action.

Incidentally, 4-hydroxy-2-cyclopenten-1-one may be prepared by a chemical synthetic method. Examples of the known synthetic method are a method by N. Tanaka, et al. [*Tetrahedron*, 32, 1713 (1976)], a method by M. Nara, et al. [*Tetrahedron*, 36, 3161 (1980)] and a method by M. Gill, et al. [*Australian Journal of Chemistry*, 34, 2587 (1981)]. However, those methods are complicated consisting of many synthetic steps and the yields are low as well whereby they are not the methods having a high efficiency. In view of the above, the present inventors have found that, when 4-cyclopenten-1,3-dione is reduced with cerium chloride (III) and sodium borohydride, it is now possible to give 4-hydroxy-2-cyclopenten-1-one in a single step in a high yield. Thus, the present invention offers an industrial method or the synthesis of 4-hydroxy-2-cyclopenten-1-one.

When 4-hydroxy-2-cyclopenten-1-one, optically active substance thereof and/or salt thereof are/is made to react with an SH-containing compound, the compound represented by the already-mentioned formula [I] (hereinafter, referred to as a thio derivative) is produced in the reaction solution.

There is no limitation at all for the compound containing an SH group and its examples are methanethiol, butanethiol, mercaptoethanol, amino acid containing an SH group and amino acid derivative containing an SH group. Examples of the amino acid containing an SH group are cysteine and homocysteine.

Examples of the amino acid derivative containing an SH group are derivatives of the above-mentioned amino acids such as cysteine derivatives, peptides containing cysteine and peptides containing cysteine derivatives. There is no particular limitation for the peptide containing cysteine so far as cysteine is a constituting component in the peptide. The peptide containing cysteine covers from low molecular substances such as oligopeptides (e.g. glutathione) to high molecular ones such as protein. Peptide containing cystine or homocystine may also be used as the peptide containing cysteine or homocysteine under the condition where it gives peptide cysteine or homocysteine during the reaction such as by combining with a reducing treatment. Incidentally, the peptide containing cysteine covers that which contains saccharide, lipid, etc. as well. In addition, it may be salt, acid anhydride, ester, etc. of the above-mentioned various substances as well.

To sum up, 4-hydroxy-2-cyclopenten-1-one reacts with a compound containing an SH group forming a thio derivative.

The means for purification and isolation of the thio derivative or optically active substance thereof which is prepared by the reaction of 4-hydroxy-2-cyclopenten-1-one, optically active substance thereof and/or a salt thereof with a compound containing an SH group such as amino acid containing an SH group or a derivative thereof may be known purifying means such as chemical method and physical method. Thus, conventionally known methods such as gel filtration, fractionation using a molecular weight fractionating membrane, extraction with solvent, fractional distillation and various chromatographic methods using ion exchange resin, etc. are combined whereby the compound of the present invention or an optically active substance thereof or a salt thereof can be purified and isolated.

For example, when equimolar 4-hydroxy-2-cyclopenten-1-one and glutathione (reduced type) are made to react, the thio derivative represented by the following formula [II] is formed in the reaction solution and, as a result of silica gel column chromatography of the reaction products containing said derivative, said thio derivative can be purified and isolated.

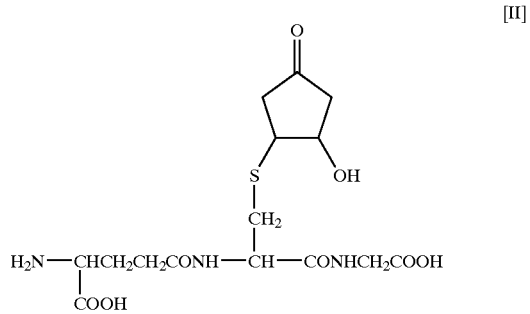

[II]

Separation of the optically active substance of the thio derivative can be conducted by subjecting the racemic mixture to mechanical resolution, preferential crystallization, resolution by crystallization as diastereomer salts or as inclusion compounds, dynamic resolution using enzymes or microorganism, resolution by means of chromatography, etc.

Gas chromatography, liquid chromatography, thin layer chromatography, etc. may be used in the case of a resolution by chromatography and a chiral stationary phase which is suitable for each of them may be used.

A method using a chiral stationary phase, a method using a chiral eluate, separation as a diastereomer, etc. may be used in an optical resolution by liquid chromatography.

A stationary phase of an amide type, that of a urea type, that of a ligand exchange type, polysaccharide-polysaccharide derivative stationary phase, protein stationary phase, polymethacrylic acid ester stationary phase, polymethacrylamide stationary phase, etc. may be used as a chiral stationary phase.

With regard to an eluting liquid, that of a hexane type, an alcohol type, an aqueous (buffer) type, etc. may be suitably used taking the combination with the above-mentioned stationary phase into consideration.

With regard to the salt of the thio derivative or optically active substance thereof which are acceptable as pharmaceutical agents are exemplified and they may be prepared by converting by means of known methods.

The thio derivative, optically active substance thereof or a salt thereof has physiological activities such as anticancer activity, the activity for suppressing the growth of cancer cells, apoptosis-inducing activity and due to these activities it is possible to offer the pharmaceutical agents containing the thio derivative, optically active substance thereof or a salt thereof as an effective component.

EXAMPLES

The present invention will be further illustrated by way of the following examples although the present invention is never limited to those examples. Incidentally, "%" used in the examples stands for "% by weight".

Example 1

The pH's of a 1M aqueous solution of L(+)-arabinose (manufactured by Wako Pure Chemical; 010-04582)), a 1M aqueous solution of D-(−)-arabinose (manufactured by Wako Pure Chemical; 013-04572), a 1M aqueous solution of xylose (manufactured by Nacalai Tesque; 367-19) and an aqueous solution of D-ribose (sold by Nacalai Tesque; 302-10) were 5.3, 4.9, 4.4 and 4.7, respectively.

They were heated at 121° C. for four hours and their apoptosis-inducing activity to human promyelocytic leukemia HL-60 was measured as follows.

Heated and non-heated substances of each of them were sterilized by a membrane filter of 0.22 μm to prepare samples for the apoptosis-inducing activity. Those samples were diluted with aseptic distilled water to an extent of 2-, 4-, 8-, 16- and 32-fold, their activity for suppressing the cell growth to the human promyelocytic leukemia HL-60 was measured as follows and their intensity or the apoptosis-inducing activity was compared.

Thus, 10 μl of each of the diluted solutions or 10 μl of aseptic distilled water were placed in a well of a 96-well microtiter plate. Then 90 μl of an RPMI 1640 medium (manufactured by Nissui) containing 10% of fetal bovine serum (manufactured by Gibco) which contained 5000 HL-60 cells (ATCC CCL240) were added thereto and an incubation was carried out at 37° C. for 48 hours in the presence of 5% carbon dioxide gas. After observing the shape of the cells under an optical microscope, 10 μl of a phosphate-buffered aqueous saline solution containing 5 mg/ml of 3-(4,5-dimethylthiazol-2-yl)-2,5-diphenyltetrazolium bromide (MTT; manufactured by Sigma), an incubation was continued for four hours more and state of growth of cells and formation of formazan produced in the cells were observed under a microscope. Further, 100 μl of 2-propanol containing 0.04N HCl were added thereto followed by well stirring and the absorbance at 590 nm was measured and used as a degree of growth of cells (an MTT method).

The result was that, in the sections to which non-heated aqueous solution of L(+)-arabinose, aqueous solution of D-(−)-arabinose, aqueous solution of D(+)-xylose and aqueous solution of D-ribose were added, there was no difference from the water-added section (a control) in terms of cell growth whereby no apoptosis-inducing activity was noted. On the contrary, in the sections where 4-, 4-, 8- and 16-fold diluted solutions of aqueous solution of L(+)-arabinose, aqueous solution of D(−)-arabinose, aqueous solution of D(+)-xylose and aqueous solution of D-ribose which were heated at 121° C. for four hours, deformation of cells was noted under a microscope and, since the absorbance at 590 nm decreased as compared with the water-added control, an activity of suppressing the growth of cancerous cells was noted.

Example 2

(1) The pH's of a 1M aqueous solution of 2-deoxy-D-ribose (manufactured by Sigma; D2751) and a 0.1M aqueous solution of 2-deoxy-D-ribose were 4.7 and 5.4, respectively. A part of the 0.1M aqueous solution of 2-deoxy-D-ribose was taken out and adjusted to pH 7.1 with 1N NaOH. This was heated at 121° C. for four hours and an apoptosis-inducing activity to HL-60 cells was measured by a method mentioned in Example 1. Incidentally, the dilution ratios were made 2-, 4-, 8-, 16-, 32-, 64- and 128-fold.

The result was that, in the section where the non-heated aqueous solution of 2-deoxy-D-ribose was added, there was no difference from the water-added control section in terms of cell growth whereby no apoptosis-inducing activity was noted. On the other hand, suppression of cell growth was noted in the sections where 28-, 16- and 16-fold diluted solutions of a 1M aqueous solution of 2-deoxy-D-ribose, a 0.1M aqueous solution of 2-deoxy-D-ribose (pH unadjusted) and a 0.1M aqueous solution of 2-deoxy-D-ribose (pH 7.1), respectively, heated at 121° C. for four hours were added.

(2) The heat-treated product at 121° C. for four hours of a 1M aqueous solution of 2-deoxy-D-ribose obtained in Example 2-(1) was separated by the following reversed phase HPLC.

Amount of the sample injected: 40 μl

Column: YMC-Pack ODS-AM (4.6×250 mm; manufactured by YMC)

Mobile phase A: water

Mobile phase B: 80% aqueous solution of acetonitrile

Flow rate: 0.8 ml/minute

Elution: Mobile phase A (five minutes)→linear concentration gradient from mobile phase A to B (20 minutes)→mobile phase B (five minutes)

Detection: absorbance at 215 nm

Each of the fractions collected every two minutes was concentrated in vacuo and an apoptosis-inducing activity to HL-60 cells was measured by a method of Example 1. The result was that the fraction 4 (retention time: 6–8 minutes) showed a strong activity and the fraction 8 (retention time: 14–16 minutes) showed a weak activity.

(3) A reversed phase HPLC of Example 2-(2) was repeated to prepare a dry product of the fraction 4. Mass analysis of this sample was carried out using DX302 (manufactured by Nippon Denshi). Further, this sample was dissolved in heavy dimethyl sulfoxide and a nuclear magnetic resonance spectrum was measured using JNM-A500 (manufactured by Nippon Denshi).

FAB-MS m/z 117 [M+H]$^+$

In the above, glycerol was used as a matrix.

$^1$H-NMR

δ 3.44(2H, m, 5-H), 4.27(1H, m, 4-H), 4.95(1H, t, H of 5-OH), 5.32(1H, d, J=5.0 Hz, H of 4-OH), 6.20(1H, ddd, J=2.0, 8.0, 15.5 Hz, 2-H), 7.10(1H, dd, J=4.0, 15.5 Hz, 3-H), 9.55(1H, d, J=8.0 Hz, 1-H)

In the above data, chemical shift of residual proton of heavy dimethyl sulfoxide was expressed as 2.49 ppm.

Assignment numbers of the signals in $^1$H-NMR are as shown in the following formula [III].

As a result, the physical data for this sample were identical with those of trans-4,5-dihydroxy-2-pentanal and it has been clarified that this sample is trans-4,5-dihydroxy-2-pentenal represented by the following formula [III].

This sample showed strong apoptosis-inducing activity and cancer cell growth suppressing activity.

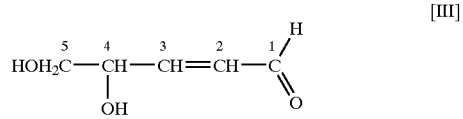

Example 3

(1) Four kinds of 100 mM deoxyribonucleotide (dATP, dGTP, dCTP and dTTP) were heated at 121° C. for four hours. Cancer cell growth suppressing activity of each of the heated samples was measured by an MTT method mentioned in Example 1.

The result was that, in a medium added with heat-treated products of dATP and dGTP up to the 16-fold diluted solutions and in a medium added with heat-treated products of dCTP and dTTP up to the 8-fold diluted solutions, numbers of viable cells were significantly reduced as compared with the water-added case. In addition, in the observation under an optical microscope, aggregation of nuclei, reduction in size of the cells and formation of apoptic body were noted in the cultured cells to which the samples were added. Incidentally, such phenomena were not noted in the cultured cells to which 10 μl of water were added (control).

(2) Aqueous solutions of five kinds of deoxyribonucleotide (deoxyadenosine, deoxyguanosine, deoxycytidine, deoxythymidine and deoxyuridine) were prepared and heated at 121° C. for four hours. Since solubility of each of them is different, concentrations of the aqueous solutions were 25 mM for deoxyadenosine, 25 mM for deoxyguanosine, 1M for deoxycytidine, 0.4M for deoxythymidine and 1M for deoxyuridine.

The cancer cell growth suppressing activity of each of the heated samples was measured by an MTT method mentioned in Example 1. The result was that viable cell numbers were significantly reduced in the media where up to 2-fold diluted solution (1.25 M based upon deoxyribonucleoside) of heat-treated deoxyadenosine solution, up to 4-fold diluted solution (0.625 M based upon deoxyribonucleoside) of heat-treated deoxyguanosine solution, up to 128-fold diluted solution (0.78 mM based upon deoxyribonucleoside) of heat-treated deoxycytidine solution, up to 16-fold diluted solution (2.5 mM based upon deoxyribonucleoside) of heat-treated deoxythymidine solution or up to 64-fold diluted solution (1.56 mM based upon deoxyribonucleoside) of heat-treated deoxyuridine solution was added as compared with the medium where only water was added. Further, in an observation under an optical microscope, aggregation of nuclei, reduction in size of the cells and formation of apoptic body were confirmed in the cultured cells to which the sample was added. Incidentally, such phenomena were not noted in the cultured cells to which 10 μl of water were added (control).

(3) Each of the heated solutions prepared in Example 3-(2) was separated by means of an HPLC under the following conditions.

Column: TSK gel ODS-80Ts (5 μm) (20 mm×25 cm; manufactured by Tosoh)

Mobile Phase A: 0.1% aqueous solution of trifluoroacetic acid (TFA)

Mobile Phase B: aqueous solution of 0.1% TFA/50% acetonitrile

Flow Rate: 8 ml/minute

Eluting Condition: Mobile phase A 100% for ten minutes→from mobile phase A 100% to mobile phase B 100% during 40 minutes→mobile phase 100% for ten minutes Detection: absorbance at 215 nm Each 1.5 ml of the heated solutions prepared in Example 3-(2) were subjected to an HPLC and fractionated every one minute and each fraction was concentrated, evaporated to dryness, re-dissolved in water and subjected to an MTT method mentioned in Example 1 whereupon an apoptosis-inducing activity was confirmed at the peaks of near 15–16 minutes and near 25–28 minutes in all of the heated solution samples.

(4) Comparison of the substance having a peak of near 15–16 minutes mentioned in Example 3-(3) with trans-4,5-dihydroxy-2-pentenal which was isolated and analyzed its structure already in Example 2-(3) was carried out by means of an HPLC under the following conditions.

Column: TSK gel ODS-80Ts (5 μm), 4.6×250 mm

Mobile Phase A: 0.1% aqueous solution of TFA

Mobile Phase B: aqueous solution of 0.1% TFA/50% acetonitrile

Flow Rate: 1 ml/minute

Eluting Condition: Mobile phase A 100% for ten minutes→from mobile phase A 100% to mobile phase B 100% during ten minutes→mobile phase 100% for ten minutes Detection: absorbance at 215 nm The result was that the eluting position of the active substance near 15–16 minutes was identical with that of trans-4,5-dihydroxy-2-pentenal.

Further, structural analysis of active substances near 15–16 minutes of each of the heated products was carried out by nuclear magnetic resonance ($^1$H-NMR). As a result, the active substance near 15–16 minutes was identified as trans-4,5-dihydroxy-2-pentenal.

Example 4

(1) The pH of an aqueous solution (0.25 mg/ml) of sodium salt of deoxyribonucleic acid (DNA) (manufactured by Wako Pure Chemical; 047-22491) was 8.9. A part of it was taken out and adjusted to pH 7.3 with 1N HCl. This was heated at 121° C. for four hours and the cell growth suppressing activity to HL-60 cells was measured by a method of Example 1. Incidentally, diluting ratios were 2-, 4-, 8-, 16- and 32-fold.

The result was that, in the sections where 8- and 16-diluted solutions of heat-treated (at 121° C. for four hours) aqueous solution of sodium salt of DNA (pH unadjusted) and aqueous solution of sodium salt of DNA (pH 7.3) were added, the absorbance at 590 nm were reduced as compared with the control where only water was added. Thus, a cell growth suppressing activity was noted.

(2) A 10 w/v % aqueous solution of sodium salt of DNA was heated at 121° C. for two hours and partitioned with ethyl acetate at the ratio of 1:2 to extract to ethyl acetate, the extract was evaporated in vacuo and the residue was dissolved in a 9:1 mixture of chloroform and methanol.

Silica gel for a column chromatography (manufactured by Fuji Silicia Kagaku; BW-300SP) (about 250 cm$^3$) was equilibrated with a 9:1 mixture of chloroform and methanol and charged in a column of 25 cm diameter×60 cm height and the above-prepared solution was subjected to a chromatography with a 9:1 mixture of chloroform and methanol under a pressure of 0.25 Kgf/cm$^2$ followed by fractionating every about 8 ml.

The solvent of the fraction was appropriately evaporated to substitute with a 50% aqueous solution of ethanol and the activity for suppressing the growth of cancer cells was measured by an MTT method mentioned in Example 1 except that the sample was diluted to a two-fold series using a 50% aqueous solution of ethanol and 2 µl of each of the diluted solutions or 2 µl of a 50% aqueous solution of ethanol were placed in a well of a flat-bottom 96-well microplate. Time for incubation was 16 hours.

The result was that, in the incubated cells where the fractions 65–81 or 177 were added, numbers of viable cells were significantly reduced as compared with the case where a 50% aqueous solution of ethanol was added. Further, in an observation under an optical microscope, aggregation of nuclei, reduction in size of the cells and formation of apoptic body were noted in the incubated cell where fractions 65–81 or 177 were added. Incidentally, such phenomena were not noted in the incubated cells where 2 µl of a 50% aqueous solution of ethanol were added (control).

(3) Fractions 65–81 were subjected to a thin layer chromatography and to a reversed phase HLPC and cancer cell growth suppressing activity and apoptic body formation were measured by an MTT method mentioned in Example 1 whereupon cancer cell growth suppressing activity and apoptic body inducing activity were noted.

In the thin layer chromatography, Silica gel 60F$_{254}$ (manufactured by Merck; 1.05554) was used and developed by a 9:1 mixture of chloroform and methanol and detection was conducted by an orcinol-sulfuric acid coloring reagent.

In the reversed phase HPLC analysis, TSK gel ODS-80 Ts column (4.6×250 mm; manufactured by Tosoh) was used and, after eluting with water for five minutes at a flow rate of 0.8 ml/minute, elution to a 80% aqueous solution of acetonitrile by means of a concentration gradient for 20 minutes was conducted and detection was carried out by measuring an absorbance at 206 nm.

The active substance of the above fractions 65–81 corresponded to a substance having a spot at Rf 0.42 in the thin layer chromatography and to a substance having a peak of retention time of 8.8 minutes in the reversed phase HPLC.

The fractions in which the substance of a spot of Rf 0.42 was detected were collected and the solvent was evaporated therefrom in vacuo.

The active component was further collected and purified by means of a reversed phase HPLC. TSK gel ODS-80 Ts (20 mm diameter×250 mm height; manufactured by Tosoh) was used as a column and eluted with water at a flow rate of 6.5 ml/minutes and detection was conducted by an absorbance at 206 nm. Each of the peaks was fractionated and concentrated in vacuo, activity thereof was measured by the above-mentioned MTT method and the peaks where the activity was noted were dissolved in heavy water and heavy dimethyl sulfoxide followed by subjecting to analysis by means of nuclear magnetic resonance spectrum.

The results are as given below.

$^1$H-NMR

δ 2.38 (1H, dd, J=2.0, 19.0 Hz, 5-H), 2.98 (1H, dd, J=6.5, 19.0 Hz, 5-H), 5.18 (1H, m, 4-H), 6.47 (1H, dd, J=1.5, 6.0 Hz, 2-H), 7.94 (1H, dd, J=2.5, 6.0 Hz, 3-H),

In the above data, chemical shift values of HOD was expressed as 4.65 ppm.

Assignment numbers of the signals in $^1$H-NMR are as shown in the following formula [IV].

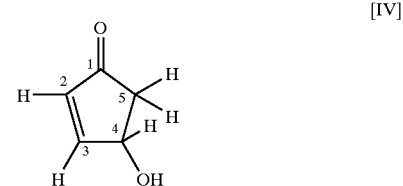

As a result, it has been clarified that this substance is 4-hydroxy-2-cyclopenten-1-one.

(4) Fraction 177 is subjected to a thin layer chromatography and to a reversed phase HLPC by the same manner as in Example 4-(3) and cancer cell growth suppressing activity and apoptic body formation were measured by an MTT method mentioned in Example 4-(2) whereupon cancer cell growth suppressing activity and apoptic body inducing activity were noted.

The active substance of the above fraction 177 corresponded to a substance having a spot at Rf 0.37 in the thin layer chromatography and to a substance having a peak of retention time of 16.8 minutes in the reversed phase HPLC.

The fraction 177 in which the substance of a spot of Rf 0.37 was detected were collected and the solvent was evaporated therefrom in vacuo.

The active component was further collected and purified by means of a reversed phase HPLC. TSK gel ODS-80 Ts (20 mm diameter×250 mm height; manufactured by Tosoh) was used as a column and eluted with water at a flow rate of 6.5 ml/minutes and detection was conducted by an absorbance at 206 nm. Each of the peaks was fractionated and concentrated in vacuo, activity thereof was measured by the above-mentioned MTT method and mass analysis of the peaks where the activity was noted was conducted using a mass spectrometer DX302 (manufactured by Nippon Denshi). m-nitrobenzyl alcohol was used as a matrix and the measurement was conducted in a positive ion mode.

FAB-MS m/z 216 [M+H]$^+$

Furthermore, a nuclear magnetic resonance spectrum was measured. Nucleomagnetic resonance spectrometer used was a JNM-A500 (manufactured by Nippon Denshi). The results are as given below.

$^1$H-NMR

δ 2.71 (1H, dd, J=3.0, 18.5 Hz, 5-H), 2.98 (1H, dd, J=7.5, 18.5 Hz, 5-H), 5.89 (1H, m, 4-H), 6.50 (1H, dd, J=2.0, 5.5 Hz, 2-H), 7.24 (2H, br-s, H of 6'-NH$_2$), 7.85 (1H, dd, J=2.5, 5.5 Hz, 3-H), 8.10 (1H, s, 2'-H), 8.14 (1H, s, 8'-H)

In the above data, the sample was dissolved in heavy dimethyl sulfoxide and chemical shift of residual proton of heavy dimethyl sulfoxide was expressed as 2.49 ppm.

Assignment numbers of the signals in $^1$H-NMR are as shown in the following formula [V].

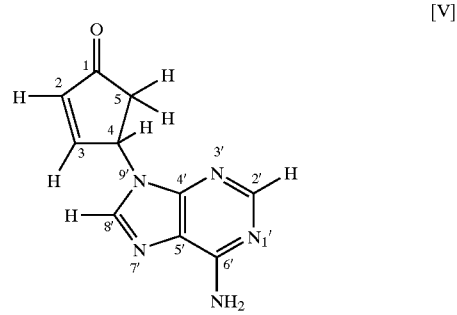

As a result, it has been clarified that this substance is 4-(9-adeninyl)-2-cyclopenten-1-one.

FIG. 1 shows a mass spectrum of 4-(9-adeninyl)-2-cyclopenten-1-one in which abscissa indicates m/z values while ordinate indicates relative intensity (%).

Figure 2:
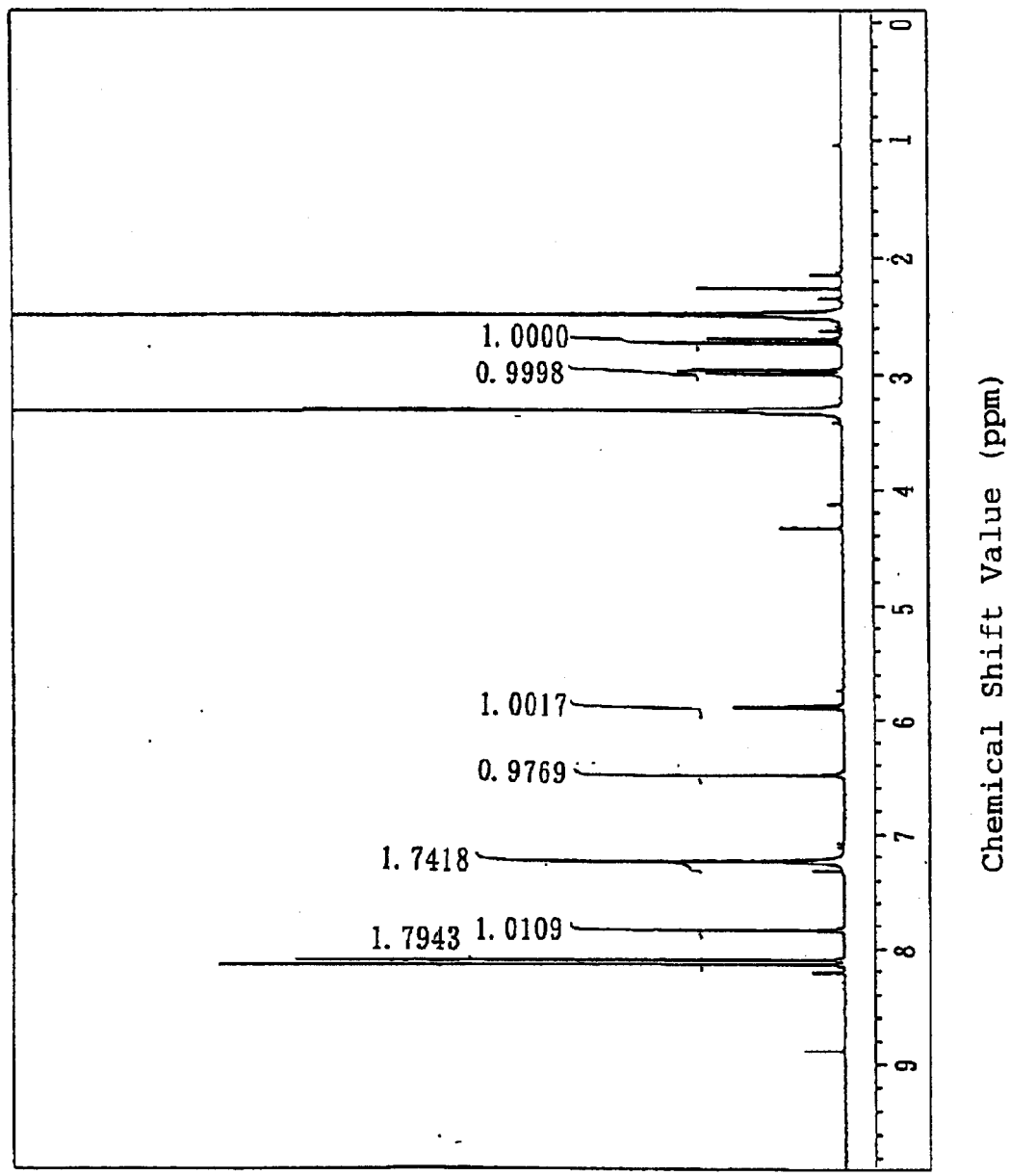
FIG. 2 shows a $^1$H-NMR spectrum of 4-(9-adeninyl)-2-cyclopenten-1-one.

FIG. 2 shows a $^1$H-NMR spectrum of 4-(9-adeninyl)-2-cyclopenten-1-one in which abscissa indicates chemical shift value (ppm) while ordinate indicates signal intensity.

(5) A 10 w/v % aqueous solution of sodium salt of DNA was heated at 121° C. for two hours. This heated solution was partitioned with ethyl acetate in a ratio of 1:2, the resulting aqueous phase was re-partitioned with a 3:1 mixture of chloroform and methanol in a ratio of 1:1, the organic solvent phase was evaporated in vacuo, a 9:1 mixture of chloroform and methanol was added thereto and the residue was removed therefrom to give a solution.

Silica gel for column chromatography (manufactured by Fuji Silicia Kagaku; BW-30SP) (about 250 cm$^3$) was equilibrated with the above mixed solution and charged in a column of 25 mm diameter×60 cm height and the above-prepared solution was developed under a pressure of 0.25 Kgf/cm$^2$ firstly with a 9:1 mixture of chloroform and methanol and secondly with a 6:1 mixture of the same and fractionated for each about 8 ml.

Each of the fractions was developed by a thin layer chromatography using a 4:1 mixture of chloroform and methanol and detected by an orcinol-sulfuric acid coloring reagent. From the fractions 380 to 500, a spot of Rf 0.36 colored in reddish brown was detected.

Fractions 400–420 were collected and the organic solvent was evaporated in vacuo and substituted with ethanol followed by subjecting to a reversed phase HPLC.

In the HPLC, TSK gel ODS-80 Ts column (20 mm diameter×250 mm height; manufactured by Tosoh) was used, eluted with a 8% aqueous solution of acetonitrile at a flow rate of 6 ml/minute for five minutes, then eluted to a 40% aqueous solution of acetonitrile with a concentration gradient method for 30 minutes, detection was conducted by means of absorbance at 206 nm and the peak of an eluting time of 35 minutes was separated.

The peak of an eluting time of 35 minutes was subjected to a reversed phase HPLC analysis and to an MTT assay using HL-60 cells.

In a reversed HPLC analysis, YMC-Pack ODS-AM column (4.6 mm diameter×250 mm height; manufactured by YMC) was used and eluted for 20 minutes at a flow rate of 0.8 ml/minute by a concentration gradient method from 4% to 25% aqueous solutions of acetonitrile and detection was conducted by means of an absorbance at 210 nm whereupon a single peak was detected at an eluting time of 14 minutes.

In an MTT assay, about 13 μg/ml of dried product of the peak of eluting time of 35 minutes showed deformation and apoptic body formation in the cells whereby cancer cell growth suppressing activity and apoptosis-inducing activity were noted.

The peak of an eluting time of 35 minutes was analyzed by means of mass analysis and by nuclear magnetic resonance spectrum after dissolving in heavy dimethyl sulfoxide.

In the mass analysis, DX 302 mass spectrometer was used. Glycerol was used as a matrix and the measurement was conducted in a positive ion mode.

FAB-MS m/z 232 [M+H]$^+$

Nucleomagnetic resonance spectrometer used was a JNM-A500. The sample was dissolved in heavy dimethyl sulfoxide and chemical shift of residual proton of heavy dimethyl sulfoxide was expressed as 2.49 ppm.

$^1$H-NMR

σ 2.61 (1H, dd, J=3.5, 18.5 Hz, 5-H), 2.91 (1H, dd, J=7.0, 18.5 Hz, 5-H), 5.65 (1H, m, 4-H), 6.42 (2H, br-s, H of 2'-NH$_2$), 6.46 (1H, dd, J=2.0, 6.0 Hz, 2-H), 7.65 (1H, s, 8'-H), 7.81 (1H, dd, J=2.5, 6.0 Hz, 3-H)

Assignment numbers of the signals in $^1$H-NMR are as shown in the following formula [VI].

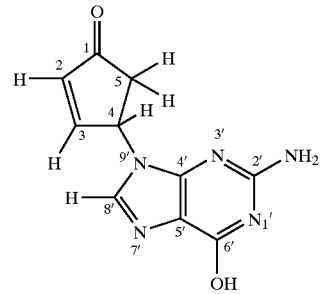

[VI]

As a result, it has been clarified that this substance is 4-(9-guaninyl)-2-cyclopenten-1-one.

Figure 3:
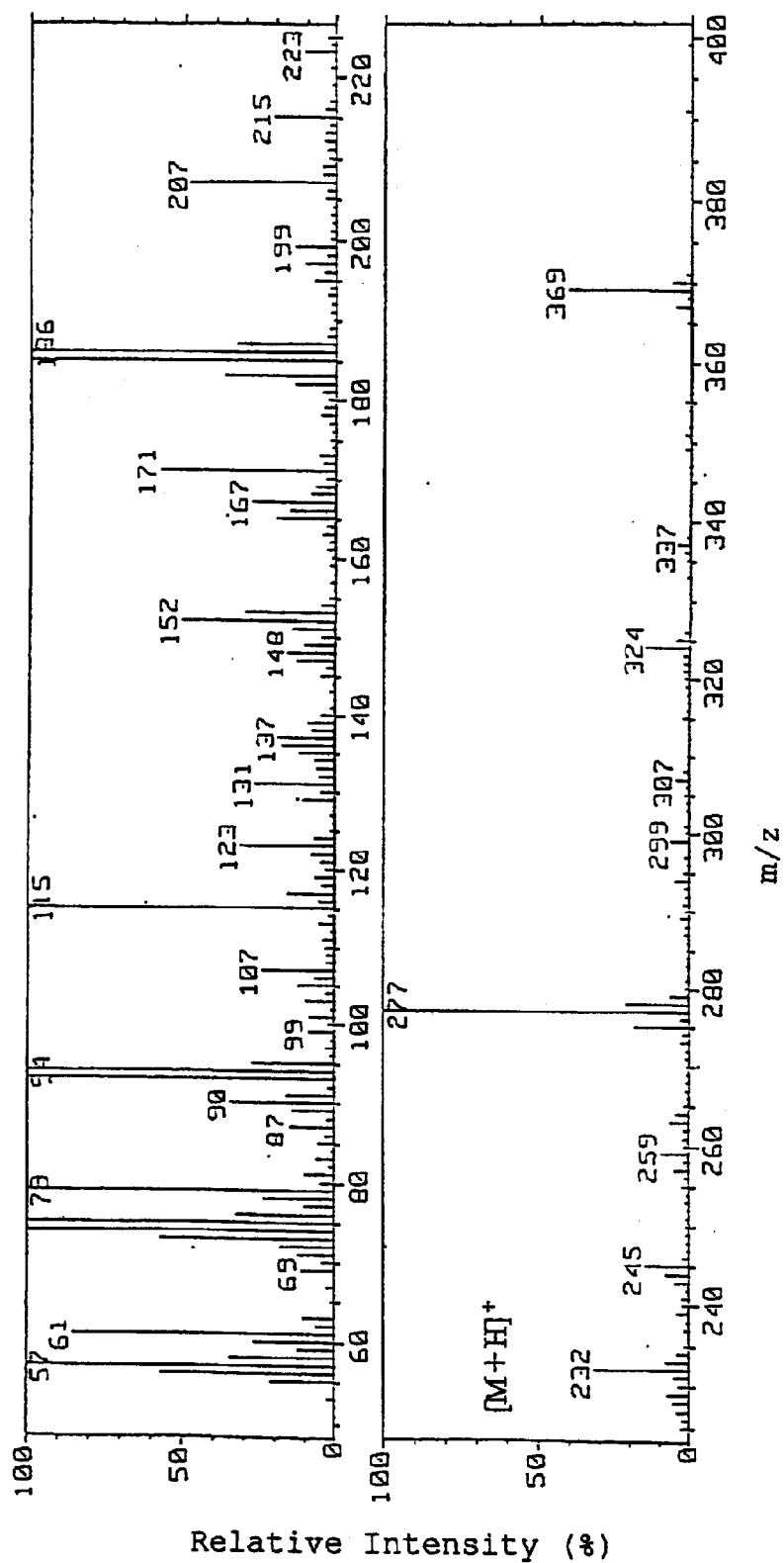
FIG. 3 shows a mass spectrum of 4-(9-guaninyl)-2-cyclopenten-1-one.

FIG. 3 shows a mass spectrum of 4-(9-guaninyl)-2-cyclopenten-1-one in which abscissa indicates m/z values while ordinate indicates relative intensity (%).

Figure 4:
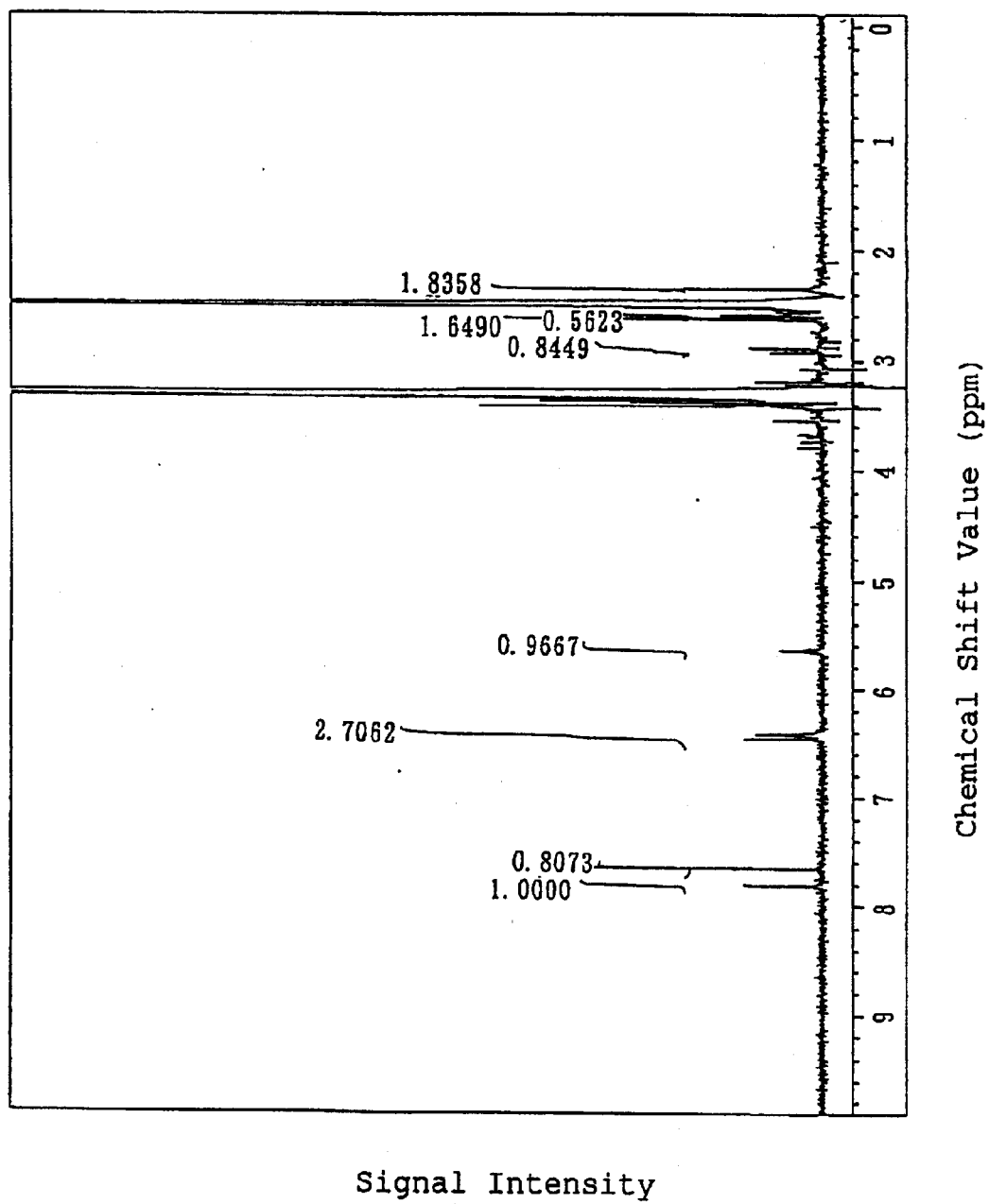
FIG. 4 shows a $^1$H-NMR spectrum of 4-(9-guaninyl)-2-cyclopenten-1-one.

FIG. 4 shows a $^1$H-NMR spectrum of 4-(9-guaninyl)-2-cyclopenten-1-one in which abscissa indicates chemical shift value (ppm) while ordinate indicates signal intensity.

Example 5

(1) A 2M aqueous solution of D-ribose (manufactured by Nacalai Tesque; 302-10) was heated at 121° C. for four hours. This heated solution was concentrated in vacuo, partitioned with ethyl acetate at the ratio of 1:2 to extract to ethyl acetate, then ethyl acetate was evaporated in vacuo from the extract and the residue was dissolved in a 9:1 mixture of chloroform and methanol.

Silica gel for column chromatography (manufactured by Fuji Silicia Kagaku; BW-300SP) (about 250 cm$^3$) was equilibrated with a 9:1 mixture of chloroform and methanol and charged in a column of 25 mm diameter×60 cm height and the above-prepared solution was developed by means of chromatography using a 9:1 mixture of chloroform and methanol with a pressure of 0.2 Kgf/cm$^2$ and fractionated every about 8 ml. Solvent of the fractions was evaporated appropriately and substituted with a 50% aqueous solution of ethanol and activity for suppressing the growth of cancer cells was measured by an MTT method mentioned in Example 4-(2).

The result was that the cultured cells where fractions 28–36 were added showed a significant reduction in the viable cell numbers as compared with the case where a 50% aqueous solution of ethanol was added. Further, in the observation under an optical microscope, aggregation of nuclei, reduction in size of the cells and formation of apoptic body were confirmed in the cultured cells where the fractions 28–36 were added. Incidentally, such phenomena were not noted in the cultured cells where 2 μl of a 50% aqueous solution of ethanol were added (control).

(2) Fractions 28–36 are subjected to a thin layer chromatography and to a reversed phase HLPC by the same manner as in Example 4-(3) and cancer cell growth suppressing activity and apoptic body formation were measured by an MTT method mentioned in Example 4-(2) whereupon cancer cell growth suppressing activity and apoptic body inducing activity were noted.

The active substance of the above fractions 28–36 corresponded to a substance having a spot at Rf 0.44 in the thin layer chromatography and to a substance having a peak of retention time of 9.7 minutes in the reversed phase HPLC.

The fractions 28–36 in which the substance of a spot of Rf 0.44 was detected were concentrated in vacuo, and were subjected to a reversed phase HLPC whereupon a single peak was detected at a retention time of 9.7 minutes.

In the mass analysis, DX 302 mass spectrometer was used. Thioglycerol was used as a matrix and the measurement was conducted in a positive ion mode.

FAB-MS m/z 115 $[M+H]^+$

97 $[M-H_2O+H]^+$

79 $[M-2H_2O+H]^+$

Furthermore, a nuclear magnetic resonance spectrum was measured. Nucleomagnetic resonance spectrometer used was a JNM-A500. The results are as given below.

$^1$H-NMR

δ 4.27 (1H, ddd, J=2.0, 4.0, 19.5 Hz, 5-H), 4.51 (1H, td, J=2.5, 19.5 Hz, 5-H), 4.93 (1H, d, J=6.0 Hz, 1-H), 6.02 (1H, m, 3-H), 7.23 (1H, ddd, J=2.5, 4.0, 10.0 Hz, 4-H), 7.26 (1H, d, J=6.0 Hz, H of 1-OH)

In the above data, the sample was dissolved in heavy dimethyl sulfoxide and chemical shift of residual proton of heavy dimethyl sulfoxide was expressed as 2.49 ppm.

Assignment numbers of the signals in $^1$H-NMR are as shown in the following formula [VII].

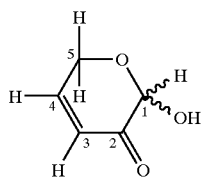

[VII]

As a result, it has been clarified that this substance is 1,5-epoxy-1-hydroxy-3-penten-2-one.

Figure 5:
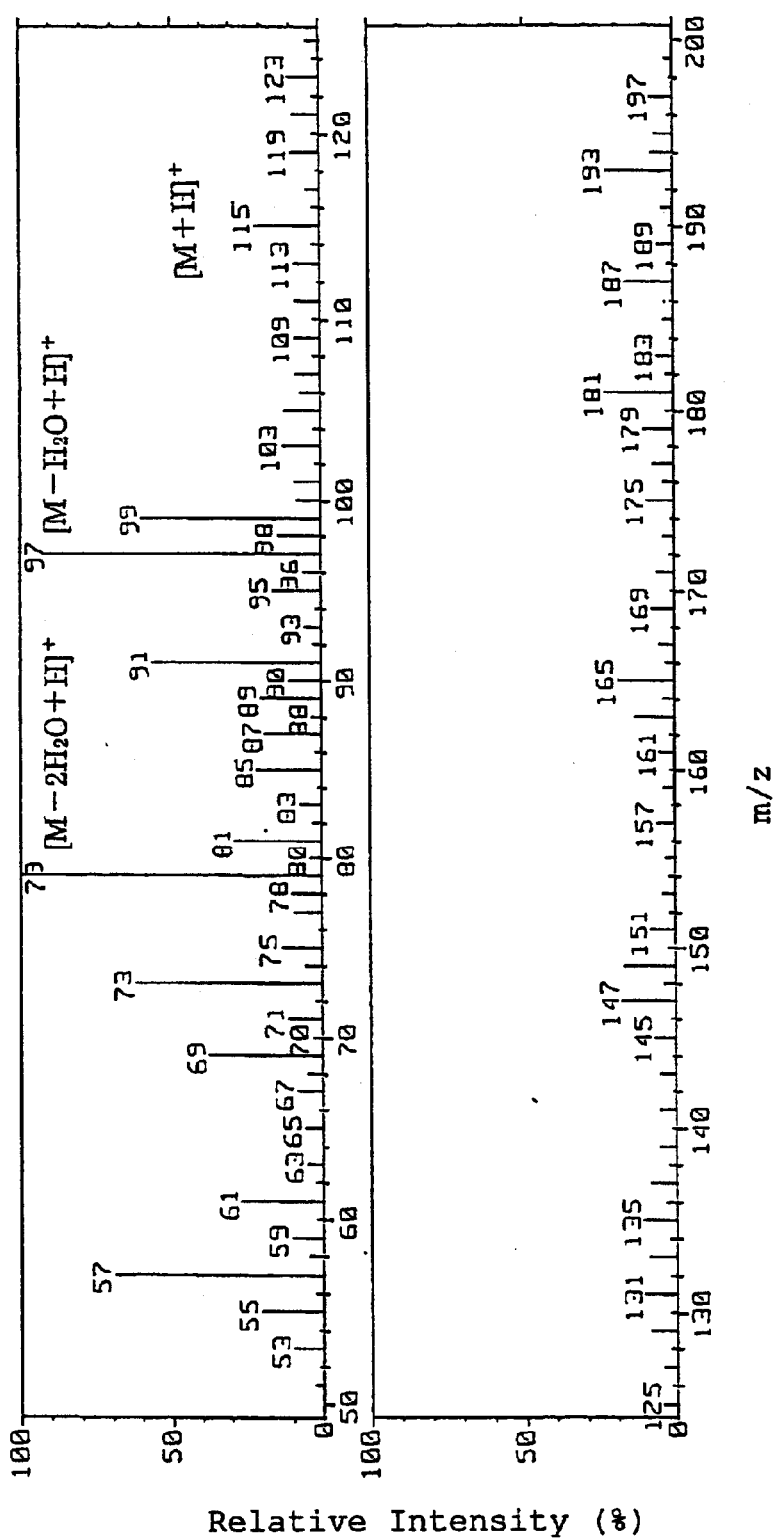
FIG. 5 shows a mass spectrum of 1,5-epoxy-1-hydroxy-3-penten-2-one.

FIG. 5 shows a mass spectrum of 1,5-epoxy-1-hydroxy-3-penten-2-one in which abscissa indicates m/z values while ordinate indicates relative intensity (%).

Figure 6:
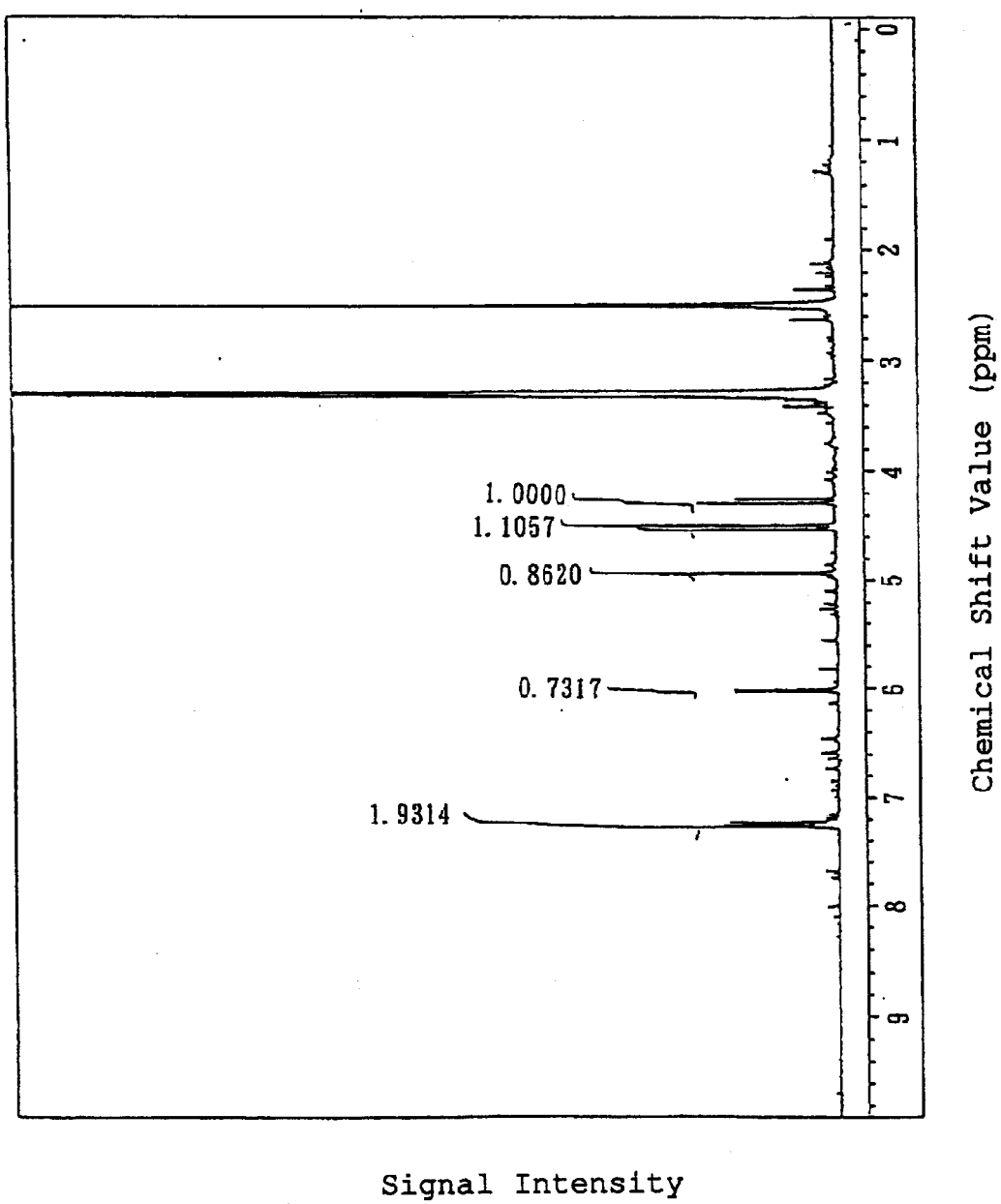
FIG. 6 shows a $^1$H-NMR spectrum of 1,5-epoxy-1-hydroxy-3-penten-2-one.

FIG. 6 shows a $^1$H-NMR spectrum of 1,5-epoxy-1-hydroxy-3-penten-2-one in which abscissa indicates chemical shift value (ppm) while ordinate indicates signal intensity.

Example 6

(1) A 2M aqueous solution of 2-deoxy-D-ribose (manufactured by Sigma; D2851) was heated at 121° C. for four hours. This heated solution (5 ml) was evaporated in vacuo and the residue was dissolved in a 98:2 mixture of chloroform and methanol.

Silica gel for chromatography (manufactured by Fuji Silicia Kagaku; BW-300SP) (about 250 cm$^3$) was equilibrated with the above mixture and charged in a column of 25 mm diameter×60 cm height and the above-prepared solution was chromatographed with a 98:2 mixture of chloroform and methanol with a pressure of 0.2 Kgf/cm$^2$ and fractionated in every about 8 ml.

Solvent of each of the fractions was evaporated and substituted with a 50% aqueous solution of ethanol and the resulting solution was subjected to a thin layer chromatography, a reverse phase HPLC analysis and an MTT assay by human promyelocytic leukemia cells (HL-60 cells).

In the thin layer chromatography, Silica gel 60F$_{254}$ (manufactured by Merck; 1.05554) was used, developed by a 9:1 mixture of chloroform and methanol and detected by an orcinol-sulfuric acid coloring reagent. In the reversed phase HPLC analysis, TSK gel ODS-80 Ts column (4.6×250 mm; manufactured by Tosoh) was used, eluted with water for five minutes at a flow rate of 0.8 ml/minute, eluted for 20 minutes to a 80% aqueous solution of acetonitrile by a concentration gradient method and detected by means of an absorbance at 206 nm.

The MTT assay was carried out by a method mentioned in Example 4-(2).

As a result of the MTT assay, a strong activity for suppressing the cell growth was noted in the fractions 48 and 88. In the fraction 48, a spot of Rf 0.52 was detected by a thin layer chromatography while a peak of retention time of 9.1 minutes was detected by a reversed phase HPLC analysis. In the fraction 88, a spot of Rf 0.35 was detected by a thin layer chromatography while a peak of retention time of 9.1 minutes was detected by a reversed phase HPLC analysis.

Those fractions were subjected to a mass analysis and to an analysis by nucleomagnetic resonance spectrum after dissolving in heavy dimethyl sulfoxide whereupon the fraction 48 was 4-hydroxy-2-cyclopenten-1-one while the fraction 88 was trans-4,5-dihydroxy-2-pentenal.

(2) An ethanolic solution of trans-4,5-dihydroxy-2-pentenal which was prepared in Example 6-(1) was allowed to stand at −40° C. in a low-temperature freezer whereupon white solid was generated.

The solid was filtered by a filter paper and washed with cold ethanol to give an ethanolic solution and a solid.

The ethanolic solution was subjected a chromatography again using a silica column. Thus, silica gel for column chromatography (manufactured by Fuji Silicia Kagaku; BW-300SP) (about 250 cm$^3$) was equilibrated with a 98:2 mixture of chloroform and methanol and chromatographed by the same mixture under a pressure of 0.2 Kgf/cm$^2$ and fractionated into about 8 ml each.

trans-4,5-Dihydroxy-2-pentenal was eluted in the fractions 90–126 while a sub-substance was eluted in the fractions 67–76.

The above solid and sub-substance were subjected to a reversed phase HPLC analysis and an MTT assay using HL-60 cells.

In the reversed phase HPLC analysis, YMC-Pack ODS-AM column (4.6 mm diameter×250 mm height; manufactured by YMC) was used, eluted with water at a flow rate of 0.8 ml/minute for five minutes, then eluted to a 80% aqueous solution of acetonitrile at a flow rate of 0.8 ml/minute by means of a concentration gradient method for 20 minutes and detected by an absorbance at 210 nm.

In the solid, a single peak was detected at an eluting time of 18 minutes while, in the sub-substance, a main peak was detected at an eluting time of 18 minutes.

In the MTT assay, deformation and apoptic body formation were noted in both solid and sub-substance whereby activity of suppressing the cell growth and activity of apoptosis induction were noted.

The solid was subjected to a mass analysis and to an analysis by nucleomagnetic resonance spectrum after dissolving in heavy dimethyl sulfoxide.

In the mass analysis, DX 302 mass spectrometer was used. Glycerol was used as a matrix and the measurement was conducted in a positive ion mode.

FAB-MS m/z 215 [M+H]$^+$

237 [M+Na]$^+$

Nucleomagnetic resonance spectrometer used was a JNM-A500. The sample was dissolved in heavy dimethyl sulfoxide and chemical shift of residual proton of heavy dimethyl sulfoxide was expressed as 2.49 ppm.

$^1$H-NMR

σ 3.30 (2H, m, 1-H), 3.80 (1H, dd, J=5.0, 8.5 Hz, 7-H), 4.01 (1H, m, 2-H), 4.05 (1H, t, J=8.5 Hz, 7-H), 4.66 (1H, t, J=6.0 Hz, H of 1-OH), 4.84 (1H, m, 6-H), 4.96 (1H, d, J=5.0 Hz, H of 2-OH), 5.31 (1H, d, J=6.5 Hz, 5-H), 5.66 (1H, ddd, J=1.5, 6.5, 15.5 Hz, 4-H), 6.01 (1H, dd, J=4.5, 15.5 Hz, 3-H), 6.21 (1H, ddd, J=1.5, 8.0, 15.5 Hz, 9-H), 7.03 (1H, dd, J=5.5, 15.5 Hz, 8-H), 9.57 (1H, d, J=8.0 Hz, 10-H)

Assignment numbers of the signals in $^1$H-NMR are as shown in the following formula [VIII].

[VIII]

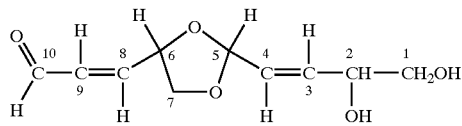

As a result, it has been clarified that this substance is 2-(trans-3,4-dihydroxy-1-butenyl)-4-(trans-2-formylvinyl)-1,3-dioxolane.

Figure 7:
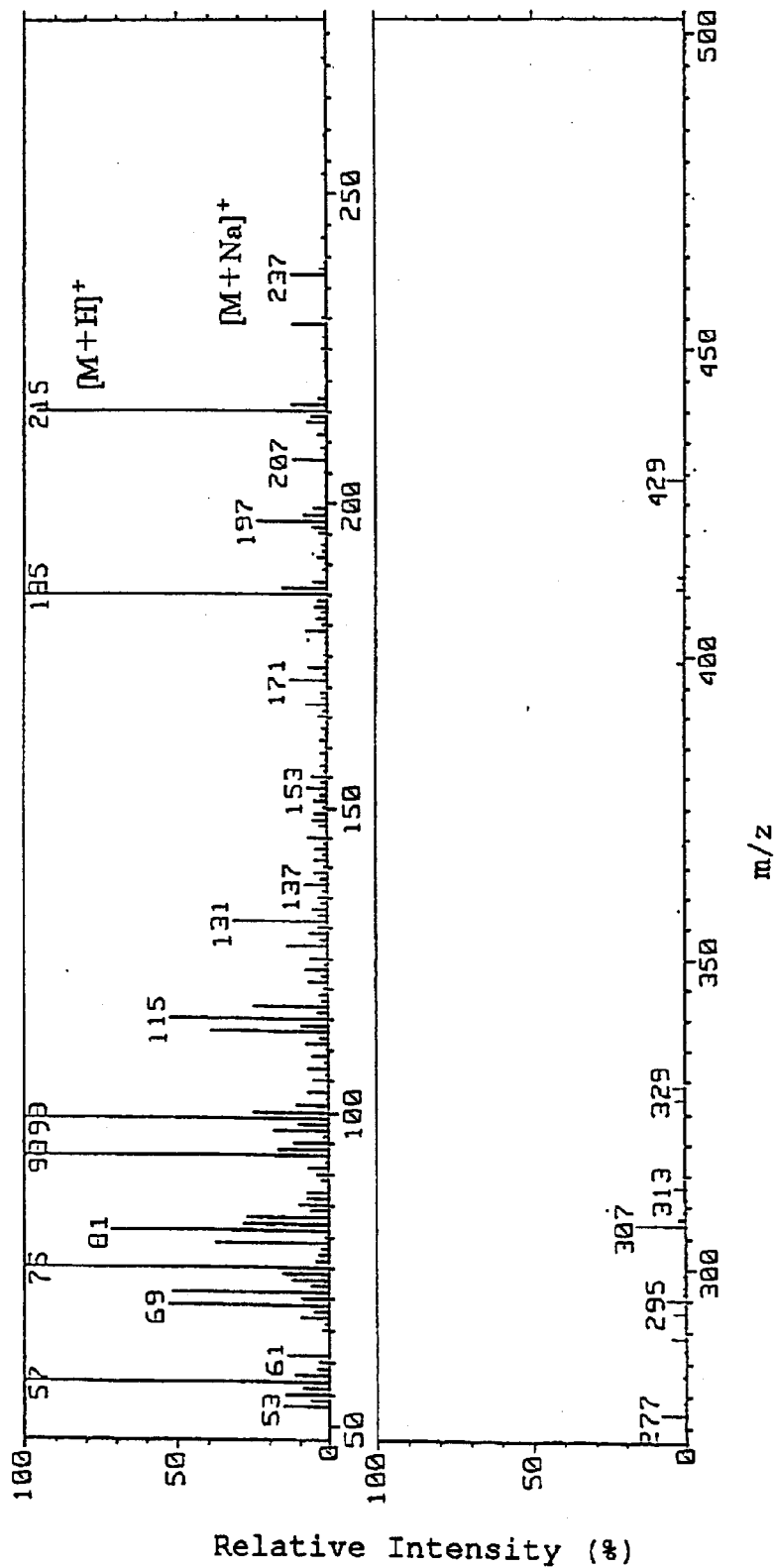
FIG. 7 shows a mass spectrum of 2-(trans-3,4-dihydroxy-1-butenyl)-4-(trans-2-formylvinyl)-1,3-dioxolane.

FIG. 7 shows a mass spectrum of 2-(trans-3,4-dihydroxy-1-butenyl)-4-(trans-2-formylvinyl)-1,3-dioxolane in which abscissa indicates m/z values while ordinate indicates relative intensity (%).

Figure 8:
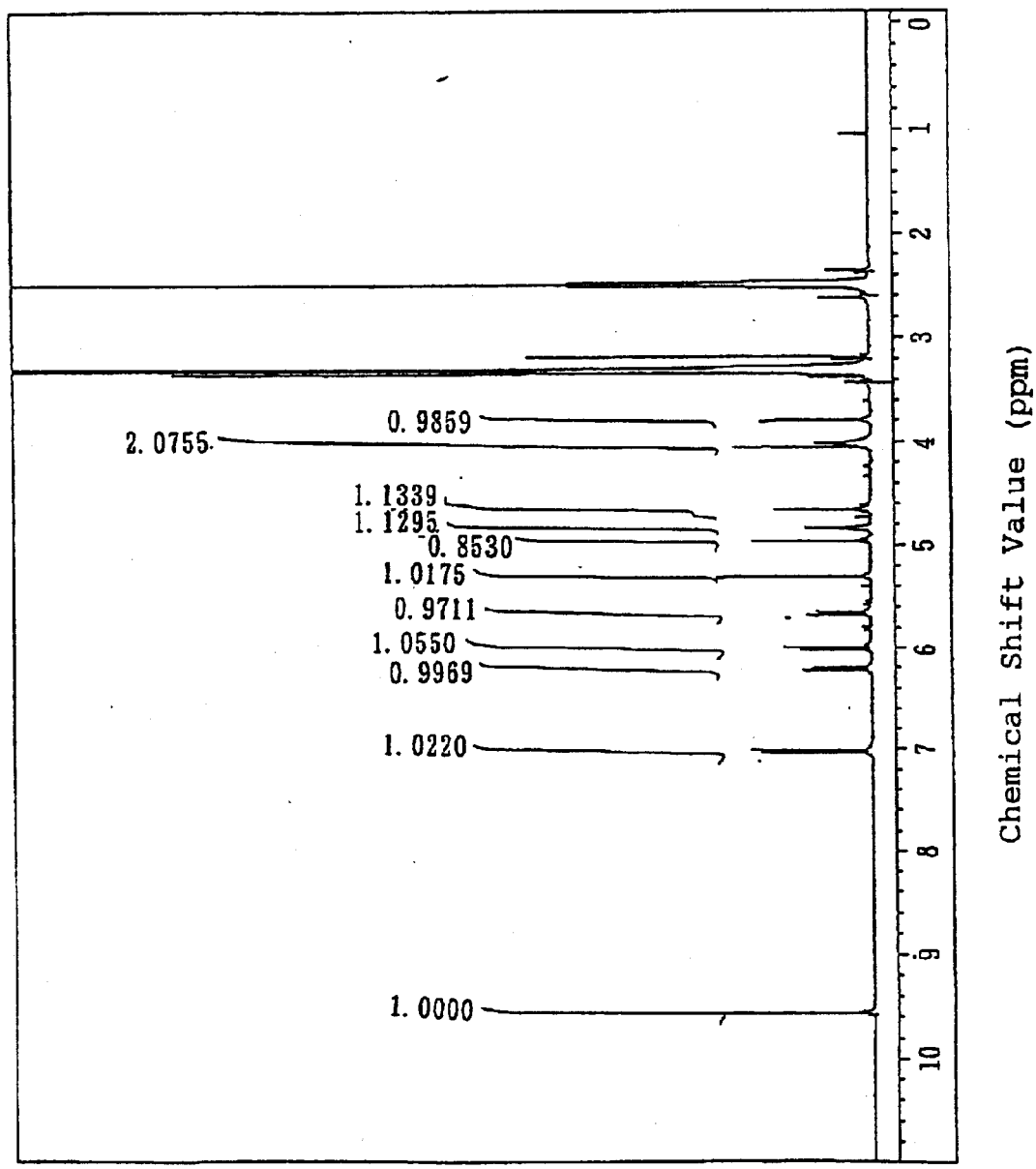
FIG. 8 shows a $^1$H-NMR spectrum of 2-(trans-3,4-dihydroxy-1-butenyl)-4-(trans-2-formylvinyl)-1,3-dioxolane.

FIG. 8 shows a $^1$H-NMR spectrum of 2-(trans-3,4-dihydroxy-1-butenyl)-4-(trans-2-formylvinyl)-1,3-dioxolane in which abscissa indicates chemical shift value (ppm) while ordinate indicates signal intensity.

(3) The concentrate of the heat-treated product mentioned in Example 6-(1) was prepared and this concentrate was subjected to a silica chromatography. Thus, silica gel for column chromatography (manufactured by Fuji Silicia Kagaku; BW-300SP) (about 250 cm$^3$) was equilibrated with a 98:2 mixture of chloroform and methanol, chromatographed with the same mixture under a pressure of 0.2 Kgf/cm$^2$ and fractionated in about 8 ml each.

Fractions 67–76 were collected, concentrated, eluted to YMC-Pack ODS-AM column (4.6 mm diameter×250 mm height; manufactured by YMC) with water at a flow rate of 0.8 ml/minute for five minutes, then eluted to a 80% aqueous solution of acetonitrile by a concentration gradient method for 20 minutes and detected by means of an absorbance at 210 nm whereupon a single peak at an eluting time of 18 minutes was obtained to give 2-(3,4-dihydroxy-1-butenyl)-4-(2-formylvinyl)-1,3-dioxolane.

Example 7

(1) D-Glucuronic acid (manufactured by Sigma; G 5269) (10 g) was dissolved in one liter of water, heated at 121° C. for four hours and concentrated in vacuo until about 10 ml.

An upper layer (40 ml) of a 3:2:2 mixture of butyl acetate, acetic acid and water was added thereto and mixed therewith and then the supernatant fluid obtained by centrifugation was concentrated in vacuo until about 10 ml.

The above extract was applied to silica gel BW-300 SP for column chromatography (2×28 cm; manufactured by Fuji Silicia Kagaku) and separated using an upper layer of a 3:2:2 mixture of butyl acetate, acetic acid and water as an eluent at a flow rate of 5 ml/minute with a pressure of 0.2 kg/cm$^2$ by a compressor. Fractionation was carried out so as to make one fraction 10 ml and, when a part of each of the fractions was taken and analyzed by a thin layer chromatography, fractions of from No. 61 to No. 80 contained 4,5-dihydroxy-2-cyclopenten-1-one of a high purity. Those fractions were combined, concentrated in vacuo and extracted with 40 ml of chloroform and the extract was concentrated in vacuo to give 100 mg of 4,5-dihydroxy-2-cyclopenten-1-one represented by the following formula [IX].

[IX]

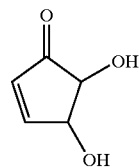

(2) Physical properties of 4,5-dihydroxy-2-cyclopenten-1-one obtained in Example 7-(1) are given below. Incidentally, mass analysis of 4,5-dihydroxy-2-cyclopenten-1-one was carried out by a DX 302 mass spectrometer (manufactured by Nippon Denshi). In the measurement of NMR spectrum using a heavy chloroform solvent, a JNM-A500 (manufactured by Nippon Denshi) was used. Specific rotation, UV absorption spectrum and infrared absorption spectrum (IR) were measured using a polarimeter (type DIP-370; manufactured by Nippon Bunko), a spectrophotometer (type UV-2500; manufactured by Shimadzu) and an infrared spectrophotomer (type FTIR-8000; manufactured by Shimadzu), respectively.

FAB-MS m/z 115 [M+H]$^+$

Glycerol was used as a matrix.

$^1$H-NMR (CDCl$_3$)

δ 4.20 (1H, d, J=2.4 Hz, 5-H), 4.83 (1H, m, 4-H), 6.30 (1H, dd, J=1.2, 6.1 Hz, 2-H), 7.48 (1H, dd, J=2.1, 6.1 Hz, 3-H)

In the above data, the chemical shift value of the $^1$H-NMR was given on a basis that the chemical shift value of CHCl$_3$ was 7.26 ppm.

Optical rotation: $[\alpha]_D^{20}$ 0$^c$ (c 1.3, water)

IR (KBr method): absorptions were noted at 3400, 1715, 1630, 1115, 1060, 1025 cm$^{-1}$.

UV: $\lambda_{max}$ 215 nm (water)

This fraction was separated by a normal phase HPLC using a column of Palpack type S and detected by means of ultraviolet absorption a 215 nm whereupon the purity was 98%.

(3) A 2M aqueous solution of D-ribose (sold by Nacalai Tesque; 302-10) or a 2M aqueous solution of D-(+)-xylose (manufactured by Nacalai Tesque; 367-19) was heated at 121° C. for 14 hours. The heat-treated solution (90 μl) was made to react with 10 μl of a 1M ethanolic solution of thiophenol (manufactured by Nacalai Tesque; 338-01) at 37° C. for 30 minutes. The heat-treated solution and its reaction product with thiophenol were analyzed by the following reversed phase HPLC.

Column: YMC-Pack ODS-AM (4.6×250 mm; manufactured by YMC)

Mobile phase A: 0.1% aqueous solution of trifluoroacetic acid (TFA)

Mobile phase B: aqueous solution containing 0.1% TFA and 80% acetonitrile

Flow rate: 0.8 ml/minute

Elution: mobile phase A (for five minutes)→linear concentration gradient from mobile phase A to mobile phase B (for 20 minutes)→mobile phase B (for five minutes)

Detection: absorbance at 215 nm

Amount of the sample injected: 10 µl

When the heat-treated solution was analyzed, a peak of retention time of 6.5 minutes was noted in both ribose and xylose. This coincides with the retention time of 4,5-dihydroxy-1-cyclopenten-1-one obtained in Example 7-(1).

When the reaction product of the heat-treated solution with thiophenol was analyzed, the peak of retention time of 6.5 minutes disappeared in both ribose and xylose and a peak of retention time of 19.6 minutes newly appeared. The newly appeared peak was identical with the peak obtained after the reaction of 4,5-dihydroxy-2-cyclopenten-1-one with thiophenol of Example 7-(1) with thiophenol.

From the above, it is apparent that 4,5-dihydroxy-2-cyclopenten-1-one is produced when ribose or xylose is heated.

Figure 9:
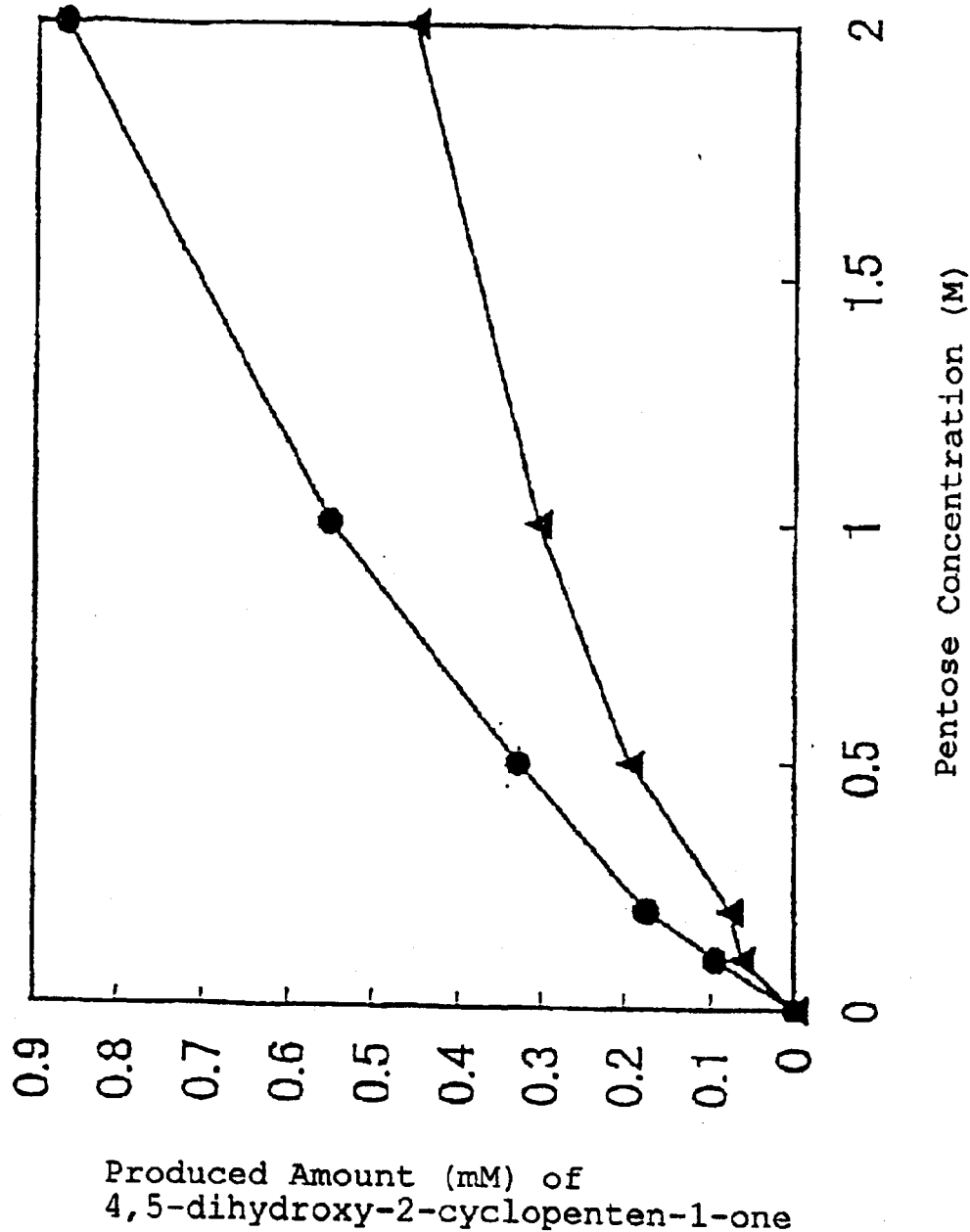
FIG. 9 shows the relation between the pentose concentration and the produced amount of 4,5-dihydroxy-2-cyclopenten-1-one.

(4) Each of 0.1M, 0.2M, 0.5M, 1M and 2M aqueous solutions of D-ribose or D-(+)-xylose was heated at 121° C. for 14 hours. This was analyzed by the same reversed phase HPLC as in Example 7-(2) and the height of the peak of retention time of 6.5 minutes was measured to determine the amount of 4,5-dihydroxy-2-cyclopenten-1-one produced. The result is given in FIG. 9. Thus, FIG. 9 shows the relation between the pentose concentration and the produced amount of 4,5-dihydroxy-2-cyclopenten-1-one where the abscissa indicates the pentose concentration (M) while the ordinate indicates the produced amount (mM) of 4,5-dihydroxy-2-cyclopenten-1-one. Incidentally, in FIG. 9, black dot is the amount of 4,5-dihydroxy-2-cyclopenten-1-one produced in the heat-treated ribose while black triangle is the amount of 4,5-dihydroxy-2-cyclopenten-1-one produced in the heat-treated D-(+)-xylose.

Example 8

(1) Sodium ribose-5-phosphase (50 mg) (manufactured by Nacalai Tesque; 302-12) was dissolved in 5 ml of water, adjusted to pH 3 by HCl and heated at 121° C. for four hours. The resulting heated product was analyzed by the following reversed phase HPLC.

Column: TSK gel ODS-80 Ts (4.6 mm×250 mm; manufactured by Tosoh)

Mobile phase: aqueous solution of TFA

Flow rate: 1 ml/minute

Detection: absorbance at 215 nm

Amount of the sample injected: 20 µl

The result was that a peak of retention time of 4.7 minutes was found and it was identical with the retention time of pure 4,5-dihydroxy-2-cyclopenten-1-one obtained in Example 7(1). Further, from the calibration curve showing the relation between the peak area and 4,5-dihydroxy-2-cyclopenten-1-one obtained from said pure 4,5-dihydroxy-2-cyclopenten-1-one, the concentration of 4,5-dihydroxy-2-cyclopenten-1-one in this heated product was calculated as 6.3 µg/ml.

This heated product (200 µl) was subjected to an HPLC by the same manner as above and a fraction of retention time of 3.8–5.8 minutes was collected. The same operation was repeated twice and the collected fraction was concentrated and evaporated in vacuo. To this was added a 4:1:1 mixture of N,O-bis(trimethylsilyl)-acetamide (manufactured by Nacalai Tesque), trimethylchlorosilane (manufactured by G. L. Science) and pyridine (manufactured by Pierce) to conduct a trimethylsilylation and the structure was analyzed by a gas chromatography/mass analysis using a mass analyzer (type DX-302; manufactured by Nippon Denshi) whereupon the mass spectrum of a peak appearing at the same retention time as the pure 4,5-dihydroxy-2-cyclopenten-1-one obtained in Example 7-(1) was identical with that of said pure 4,5-dihydroxy-2-cyclopenten-1-one.

Accordingly, production of 4,5-dihydroxy-2-cyclopenten-1-one was now confirmed.

(2) Sodium ribose-5-phosphate (30 mg) was dissolved in 3 ml of water and adjusted to pH 2.5 by 1N HCl. Amount of 4,5-dihydroxy-2-cyclopenten-1-one contained in this sample was measured by the following gel filtration HPLC.

Column: TSK-gel G2500PW (XL) (7.8×300 mm; manufactured by Tosoh)

Column temperature: 40° C.

Mobile phase: water

Flow rate: 1 ml/minute

Detection: absorbance at 215 nm

The result was that a peak of retention time of 11.4 minutes was noted and the retention time was identical with that of pure 4,5-dihydroxy-2-cyclopenten-1-one obtained in Example 7-(1). Further, from the calibration curve showing the relation between the peak area and 4,5-dihydroxy-2-cyclopenten-1-one obtained from said pure 4,5-dihydroxy-2-cyclopenten-1-one, the concentration of 4,5-dihydroxy-2-cyclopenten-1-one in this heated product was calculated as 8.9 µg/ml.

From the above, it is now apparent that, when sodium ribose-5-phosphate is heated, 4,5-dihydroxy-2-cyclopenten-1-one is produced.

Example 9

A 2M aqueous solution of D-ribose was heated at 121° C. for four hours. This heated solution was concentrated in vacuo and partitioned with ethyl acetate at the ratio of 1:2 to extract to ethyl acetate, ethyl acetate was evaporated therefrom in vacuo and the residue was dissolved in a 9:1 mixture of chloroform and methanol.

Silica gel for column chromatography (BW-30 SP manufactured by Fuji Silicia Kagaku) (about 250 cm$^3$) was equilibrated with the above mixture and charged in a column of 25 mm diameter×60 cm height and the above-prepared solution was chromatographed with a 9:1 mixture of chloroform and methanol under a pressure of 0.2 Kgf/cm$^2$ and fractionated in every about 8 ml. Solvent of the fraction was appropriately evaporated followed by subjecting to a thin layer chromatography, fractions 38–57 having a spot of Rf 0.5 were collected and the solvent was evaporated therefrom and substituted with a 50% aqueous solution of ethanol. In the thin layer chromatography, Silica gel 60F$_{254}$ was used, development was carried out by a 9:1 mixture of chloroform and methanol and detection was conducted by an orcinol-sulfuric acid coloring reagent.

After that, the active substance was separated and purified by a reversed phase HPLC. In the separation, TSK gel ODS-80 Ts column (4.6×250 mm) was used, eluted with water for ten minutes at a flow rate of 6.5 ml/minute, then eluted to a 60% aqueous solution of acetonitrile by a concentration gradient method for 15 minutes and detected by an absorbance at 206 nm. The peak of eluting time of 15 minutes was collected.

The peak of eluting time of 15 minutes was subjected to a measurement of cancer cell growth suppressing activity and apoptosis-inducing activity by an MTT method mentioned in Example 4-(2) whereupon deformation of cell and suppression of formazan formation were noted and, therefore, cell growth suppressing activity and apoptosis-inducing activity were confirmed.

The peak of retention time of 15 minutes was subjected to a reversed phase HPLC analysis. In the analysis, TSK gel ODS-80 Ts column (4.6×250 mm) was used and it was eluted with 0.8 ml/minute of water for five minutes, eluted to a 80% aqueous solution of acetonitrile by a concentration gradient method for 20 minutes and detected by means of absorbance at 206 nm. In this analysis, a peak of retention time of 15 minutes was eluted at an eluting time of 5.7 minutes and its eluting time was identical with that of 4,5-dihdyroxy-2-cyclopenten-1-one mentioned in Example 7-(1). Further, the fraction of the peak of retention time of 15 minutes was analyzed by a nuclear magnetic resonance spectrum after dissolving in heavy dimethyl sulfoxide and the spectrum of 4,5-dihydroxy-2-cyclopenten-1-one was confirmed.

Example 10

4-Cyclopenten-1,3-dione (Aldrich; code 16,168-3) (1 g; 10.4 mmoles) and 1.94 g (5.2 mmoles) of cerium chloride (III).7H$_2$O (Nacalai Tesque; code 077-20) were dissolved in 25 ml of water. NaBH$_4$ (Nacalai Tesque; code 312-29) (198 mg; 5.2 mmoles) was gradually added thereto with stirring in ice and, after completion of addition, pH was made neutral or lower by 1N HCl.

The reaction solution was subjected to a TLC using a developer which was a 9:1 mixture of chloroform and methanol and detected by orcinol-sulfuric acid whereupon a red spot was detected at around Rf 0.5. The neutralized reaction solution was concentrated in vacuo until the syrupy state, the syrup was extracted with 100 ml of a 40:1 mixture of chloroform and methanol and the extract was filtered through silica gel. The filtrate was concentrated in vacuo and purified by subjecting to a medium-pressure silica (80 g) chromatography using a 40;1 mixture of chloroform and methanol to give 236 mg (yield: 23%) of highly pure 4-hydroxy-2-cyclopenten-1-one in pale yellow oil which was confirmed from its nuclear magnetic resonance spectrum.

Example 11

A 200 mM phosphate buffer of pH 7 (2 ml) containing 50 mM 4-hydroxy-2-cyclopenten-1-one and 100 mM L-glutathione was warmed at 37° C. for one hour to prepare a sample and the sample was subjected to a reversed phase HPLC to collect the peaks. The column used was TSK gel ODS-80 Ts (20 mm diameter×250 mm height; manufactured by Tosoh). Elution was conducted with 6.5 ml/minute of distilled water and detection was conducted by an absorbance at 206 nm. The peaks were collected, concentrated in vacuo and subjected to an MTT assay using human promyelocytic leukemia cells (HL-60 cells) mentioned in Example 1.

As a result of the MTT assay, cancer cell growth suppressing activity and apoptic body production were noted in the peak 1 of retention time of 14.4 minutes and in the peak 3 of retention time of 16.6 minutes. The two peaks where the activity was noted were purified by subjecting to a chromatography again using the same column.

The two peaks where the activity was noted were analyzed by a mass analysis and a nucleomagnetic resonance spectrum.

The mass analysis was conducted by a mass spectrometer of type DX 302 (Nippon Denshi) in a positive ion mode using glycerol as a matrix.

FAB-MS of the peak 1: m/z 406 [M+H]$^+$

FAB-MS of the peak 3: m/z 406 [M+Z]$^+$

428 [M+Na]$^+$

Nucleomagnetic resonance spectrometer used was a JNM-A500 (Nippon Denshi) and the measurement was conducted by dissolving in heavy water. Chemical shift values in $^1$H-NMR when that of HOD was set at 4.65 ppm were as follows.

Peak 1; σ 2.13 (2H, m, 5'-H), 2.29 (1H, m, 2-H), 2.45 (1H, m, 5-H), 2.50 (2H, m, 4'-H), 2.65 (1H, m, 5-H), 2.69 (1H, m, 2-H), 2.90~3.00 (1H, m, 1'-H), 3.10~3.18 (1H, m, 1'-H), 3.61 (1H, m, 3-H), 3.76 (1H, m, 6'-H), 3.89 (2H, s, 9'-H), 4.50~4.62 (2H, m, 4-H, 2'-H)

Peak 3; σ 2.10 (2H, m, 5'-H), 2.27 (1H, m, 2-H), 2.29 (1H, m, 5-H), 2.48 (2H, m, 4'-H), 2.76~2.84 (1H, m, 5-H), 2.84~2.92 (1H, m, 2-H), 2.93~3.02 (1H, m, 1'-H), 3.09~3.21 (1H, m, 1'-H), 3.40 (1H, m, 3-H), 3.73 (1H, m, 6'-H), 3.86 (2H, s, 9'-H), 4.31~4.40 (1H, m, 4-H), 4.59 (1H, m, 2'-H)

Assignment numbers of the signals of peak 1 and peak 3 are as shown in the following formula [X].

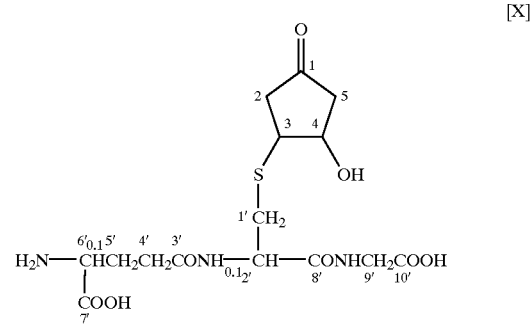

The peak 1 was a mixture of diastereomers of a 3R,4S compound and a 3S,4R compound while the peak 3 was a mixture of diastereomers of a 3R,4R compound and a 3S,4S compound.

From the above, it was apparent that the peak 1 of the present sample was cis-3-L-glutathion-s-yl-4-hydroxy-2-cyclopenten-1-one where 3- and 4-positions were in cis while the peak 3 of the present sample of trans-3-L-glutathion-s-yl-4-hydroxy-2-cyclopenten-1-one where 3- and 4-positions were in trans.

Figure 10:
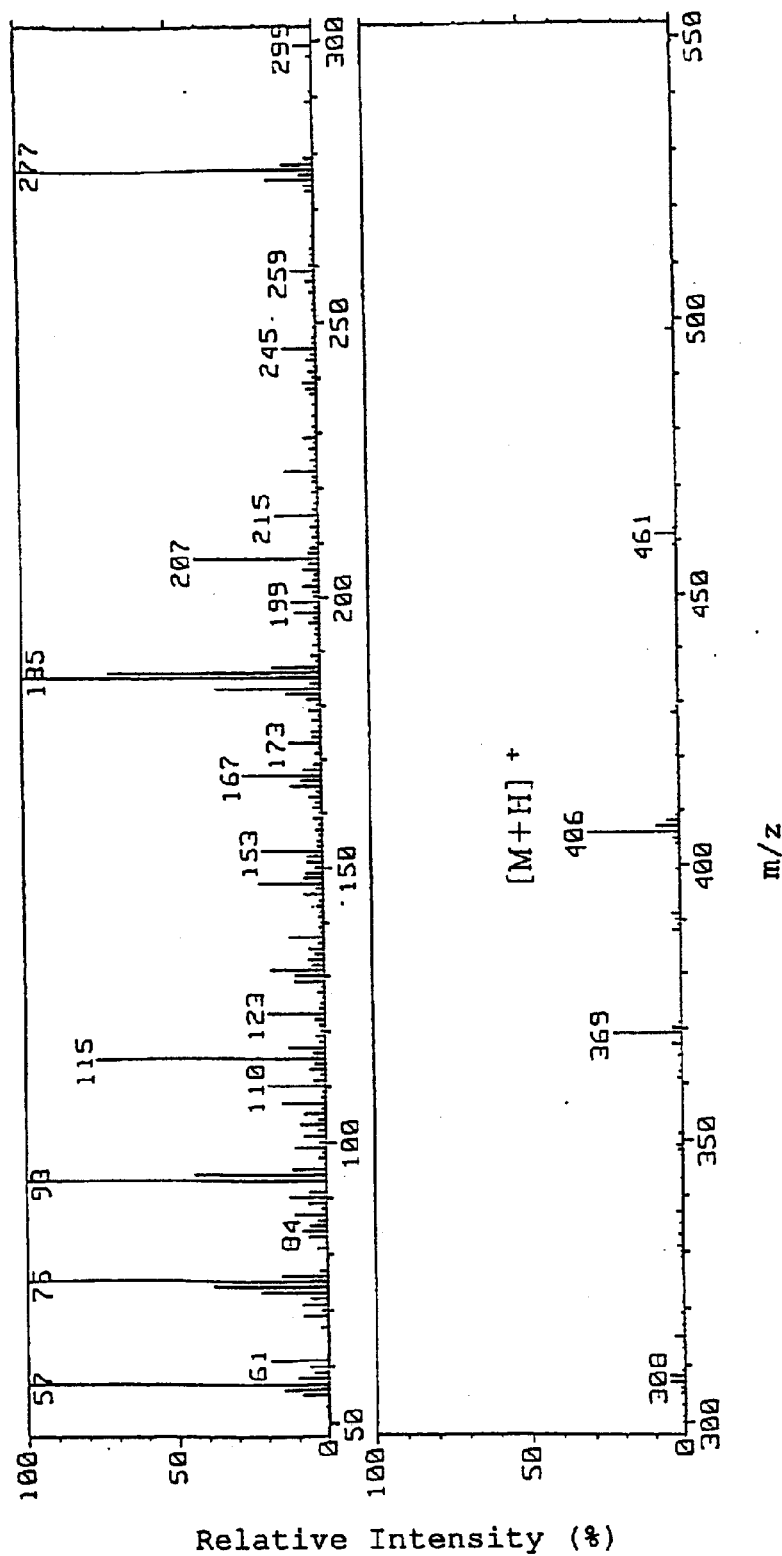
FIG. 10 shows a mass spectrum of the peak 1.

FIG. 10 shows a mass spectrum of the peak 1 in which the abscissa indicates m/z while the ordinate indicates a relative intensity (%).

Figure 11:
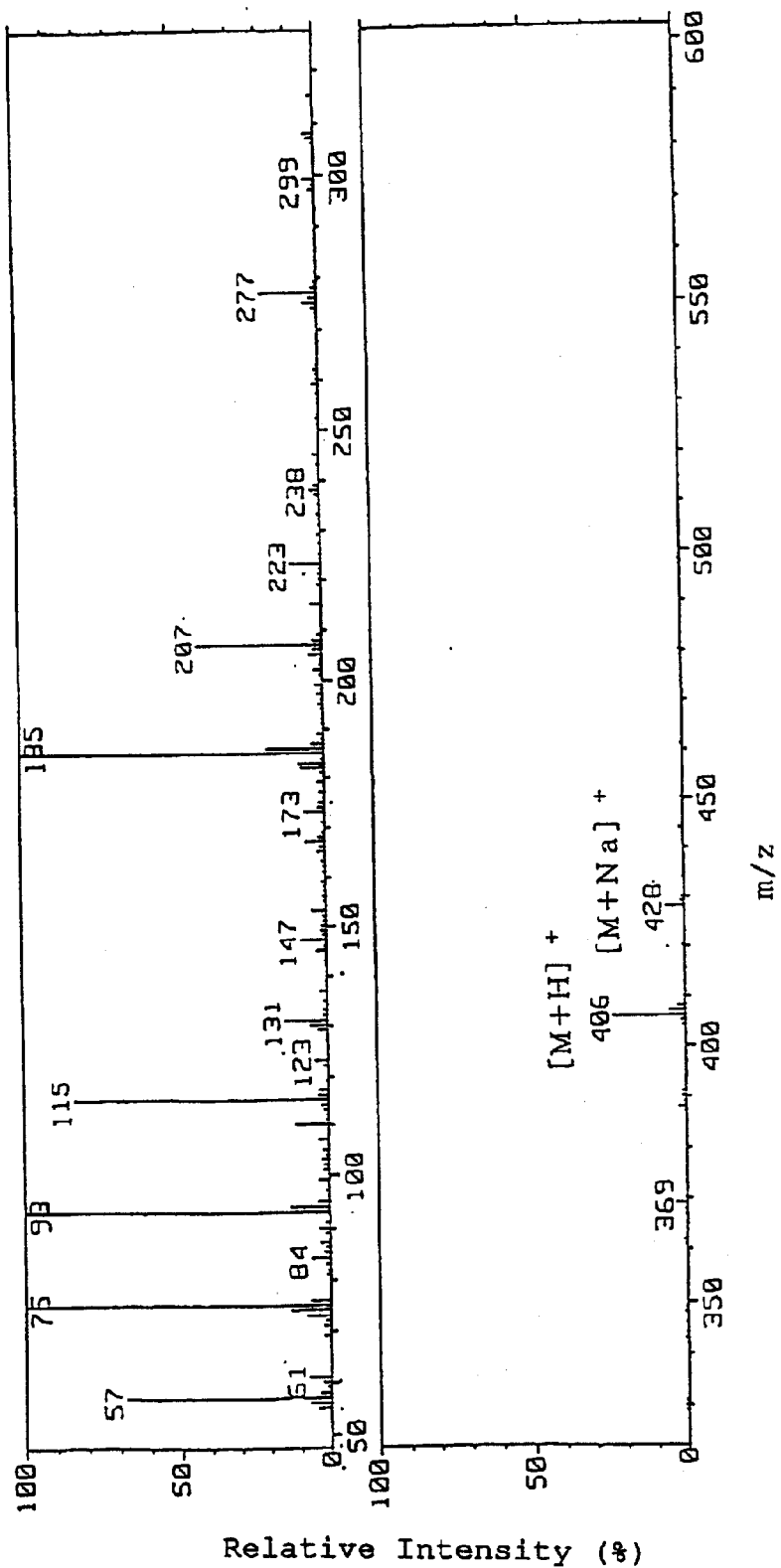
FIG. 11 shows a mass spectrum of the peak 3.

FIG. 11 shows a mass spectrum of the peak 3 in which the abscissa indicates m/z while the ordinate indicates a relative intensity (%).

Figure 12:
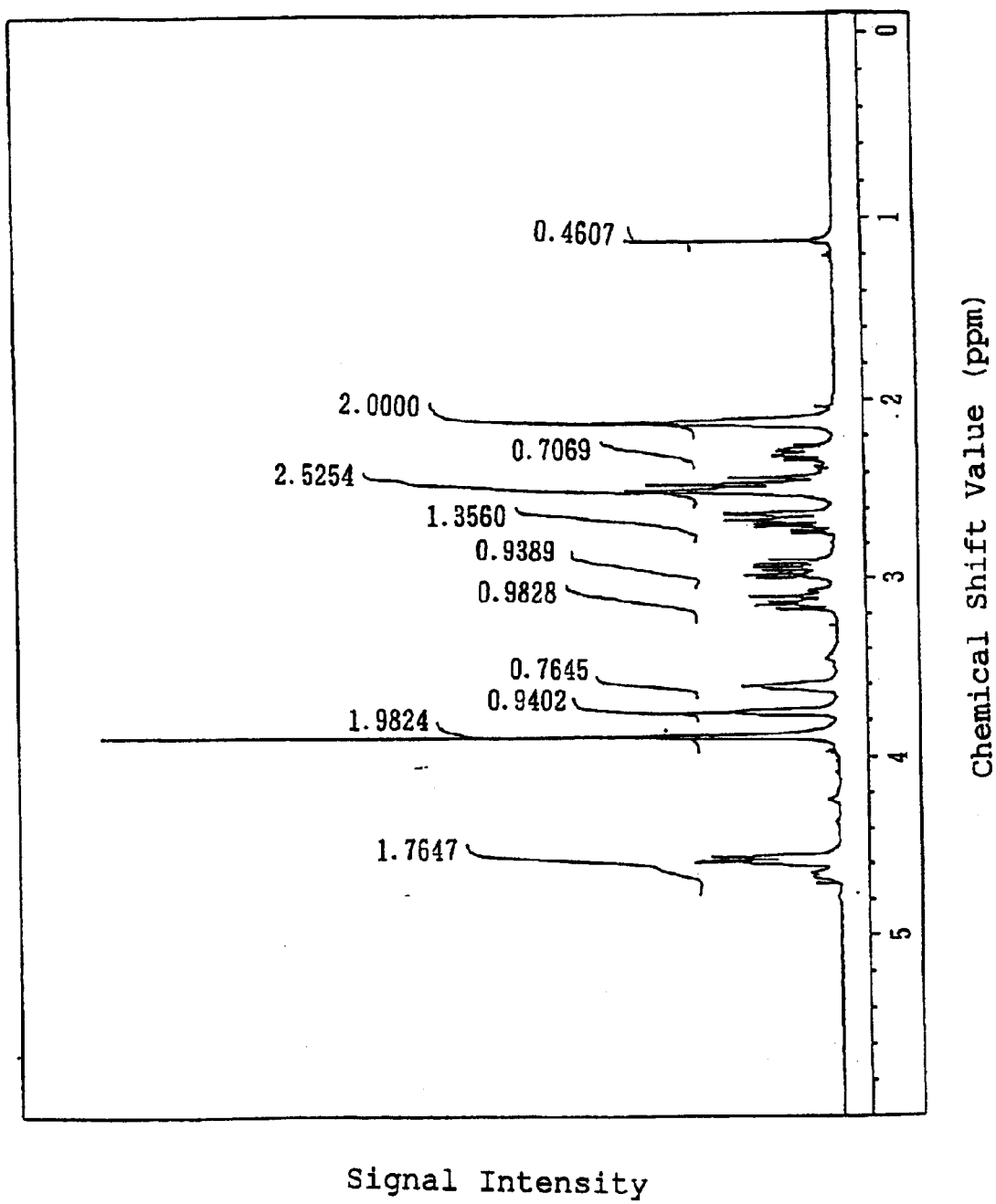
FIG. 12 shows a $^1$H-NMR spectrum of the peak 1.

FIG. 12 shows a $^1$H-NMR spectrum of the peak 1 in which the abscissa indicates chemical shift value (ppm) while the ordinate indicates a signal intensity.

Figure 13:
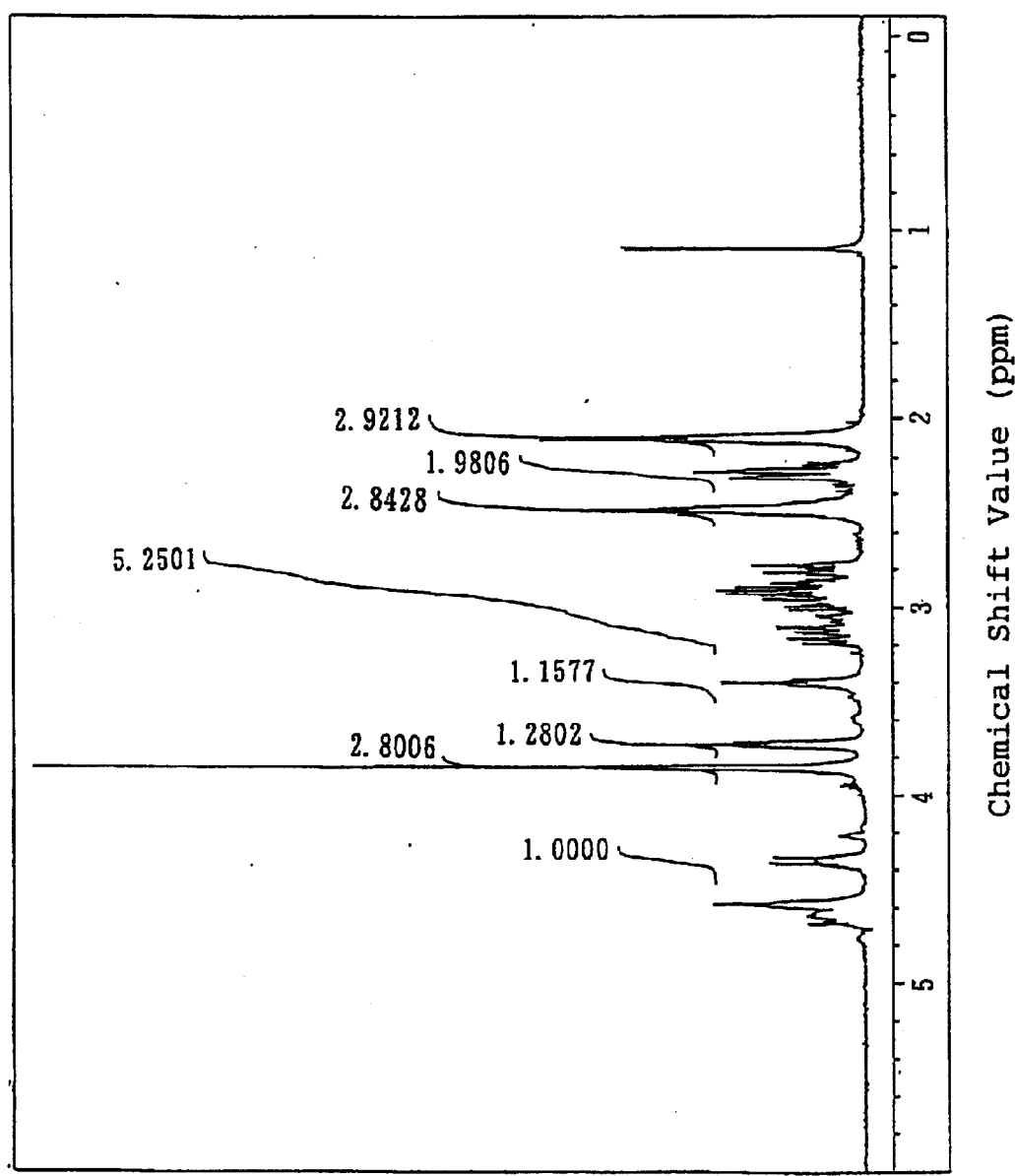
FIG. 13 shows a $^1$H-NMR spectrum of the peak 3.

FIG. 13 shows a $^1$H-NMR spectrum of the peak 3 in which the abscissa indicates chemical shift value (ppm) while the ordinate indicates a signal intensity.

Example 12

(1) HL-60 cells (ATCC CCL-240) incubated at 37° C. in an RPMI 1640 medium (manufactured by BioWhittaker) containing 10% of fetal bovine serum (manufactured by JRH) treated at 56° C. for 30 minutes were suspended in an RPMI 1640 medium to make the concentration $2.5 \times 10^5$ cells/5 ml.

To 5 ml of this suspension were added 10 µl of 12.5 mM, 25 mM, 50 mM or 100 mM of a 70% ethanolic solution of 4,5-dihydroxy-2-pentenal prepared in Example 6-(1), 0.05 mM, 0.5 mM, 5 mM or 50 mM of a 70% ethanolic solution of 4-hydroxy-2-cyclopenten-1-ol prepared in Example 6-(1), 5 mM, 10 mM or 20 mM of a 70% ethanolic solution of 4-(9-adeninyl)-2-cyclopenten-1-one prepared in Example 4-(4), 2.5 mM, 5 mM, 15 mM or 25 mM of a 70% ethanolic solution of 4-(9-guaninyl)-2-cyclopenten-1-one prepared in Example 4-(5), 75 mM, 150 mM or 300 mM of a 70% ethanolic solution of 1,5-epoxy-1-hydroxy-3-penten-2-one prepared in Example 5-(2) or 5 mM, 25 mM or 50 mM of a 70% ethanolic solution of 2-(trans-3,4-dihydroxy-1-butenyl)-4-(trans-2-formylvinyl)-1,3-dioxolane prepared in Example 6-(2) followed by incubating at 37° C. in the presence of 5% carbon dioxide gas for 24 hours.

The incubated cells were observed under an optical microscope and aggregation of nuclei, reduction in size of the cells and formation of apoptic body were confirmed in the incubated cells where 1 µM or more final concentration of 4,5-dihydroxy-2-pentenal, 10 µM or more final concentration of 4-hydroxy-2-cyclopenten-1-one, 10 µM or more final concentration of 4-(9-adeninyl)-2-cyclopenten-1-one, 39 µM or more final concentration of 4-(9-guaninyl)-2-cyclopenten-1-one, 625 µM or more final concentration of 1,5-epoxy-1-hydroxy-3-penten-2-one or 80 µM or more final concentration of 2-(trans-3,4-dihydroxy-1-butenyl)-4-(trans-2-formylvinyl)-1,3-dioxolane was added. Incidentally, such phenomena were not noted in the incubated cells to which 10 ml of 70% ethanolic solution were added used as a control.

(2) HL-60 cells which were incubated on an RPMI 1640 medium containing 10% of fetal bovine serum processed at 56° C. for 30 minutes were suspended in an RPMI 1640 medium to make $2.5 \times 10^5$ cells/5 ml.

To 5 ml the suspension were added 10 µl of 12.5 mM, 25 mM, 50 mM or 100 mM of a 70% ethanolic solution of 4,5-dihydroxy-2-pentenal, 0.05 mM, 0.5 mM, 5 mM or 50 mM of a 70% ethanolic solution of 4-hydroxy-2-cyclopenten-1-one, 5 mM, 10 mM or 20 mM of a 70% ethanolic solution of 4-(9-adeninyl)-2-cyclopenten-1-one prepared in Example 4-(4), 2.5 mM, 5 mM, 15 mM or 25 mM of a 70% ethanolic solution of 4-(9-guaninyl)-2-cyclopenten-1-one prepared in Example 4-(5) 75 mM, 150 mM or 300 mM of a 70% ethanolic solution of 1,5-epoxy-1-hydroxy-3-penten-2-one prepared in Example 5-(2) or 5 mM, 25 mM or 50 mM of a 70% ethanolic solution of 2-(trans-3,4-dihydroxy-1-butenyl)-4-(trans-2-formylvinyl)-1,3-dioxolane prepared in Example 6-(2) followed by incubating at 37° C. in the presence of 5% of carbon dioxide gas for 24 hours and 48 hours and the resulting cells were subjected to a measurement of apoptosis cells using FACScan by a method mentioned in pages 129–130 of "Experimental Protocol Series—Apoptosis Experiment Protocol" which was an extra issue of "Saibo Kogaku (Cell Technology)" (published by Shujunsha in 1994) and also to a measurement of analysis of fragmentation of DNA by a method mentioned in page 61–63 of "Biomanual UP Series—New Experimental Methods for Apoptosis" (published by Yodosha in 1995).

The result was that apoptosis cells were confirmed in the incubated cells where 50 µM or more final concentration of 4,5-dihydroxy-2-pentenal, 10 µM or more final concentration of 4-hydroxy-2-cyclopenten-1-one, 10 µM or more final concentration of 4-(9-adeninyl)-2-cyclopenten-1-one, 20 µM or more final concentration of 4-(9-guaninyl)-2-cyclopenten-1-one, 600 µM or more final concentration of 1,5-epoxy-1-hydroxy-3-penten-2-one or 50 µM or more final concentration of 2-(trans-3,4-dihydroxy-1-butenyl)-4-(trans-2-formylvinyl)-1,3-dioxolane was added. Further, fragmentation of DNA was confirmed in the incubated cells where 50, 100 and 200 µM final concentrations of 4,5-dihydroxy-2-pentenal, 10 µM final concentration of 4-hydroxy-2-cyclopenten-1-one and 10 and 30 µM final concentrations of 4-(9-adeninyl)-2-cyclopenten-1-one were added. Incidentally, such phenomena were not noted in the control which was the incubated cells where 10 µl of a 70% ethanol solution were added thereto.

(3) The cells which were incubated for 24 hours by the same manner as in Example 9-(2) were stained with 0.4% Trypan Blue and observed under an optical microscope, numbers of viable cells which were not stained and of dead cells which were stained in blue were measured, concentration (survival rate$_{50}$) of each of the samples where survival rate becomes 50% was determined and the result is given in Table 1.

TABLE 1

| Name of Substance | Survival Rate$_{50}$ (µM) |
|---|---|
| 4,5-dihydroxy-2-pentenal | 124 |
| 4-hydroxy-2-cyclopenten-1-one | 25.5 |
| 4-(9-adeninyl)-2-cyclopenten-1-one | 22.4 |
| 4-(9-guaninyl)-2-cyclopenten-1-one | 67.9 |
| 1,5-epoxy-1-hydroxy-3-penten-2-one | 438 |
| 2-(trans-3,4-dihydroxy-1-butenyl)-4-(trans-2-formylvinyl)-1,3-dioxolane | 74.4 |

Example 13

(1) One µl of a pBR322 DNA (0.25 µg/µl) (manufactured by Takara Shuzo) was added to a mixture of 2 µl of topoisomerase II [manufactured by Topogen; 2 units/µl], 2 µl of 10-fold diluted buffer [0.5M Tris-HCl (pH 8.0), 1.2M KCl, 0.1M MgCl$_2$, 5 mM adenosine triphosphate and 5 mM dithiothreitol], 2 µl of 0.1% bovine serum albumin (manufactured by Takara Shuzo), 11 µl of distilled water and 2 µl of distilled water (a control) or 4,5-dihydroxy-2-pentenal or 4-hydroxy-2-cyclopenten-1-one made in various concentrations with water and then made to react at 37° C. After reacting for 30 minutes, the reaction was stopped by adding 2 µl of an aqueous solution of 1% sodium dodecylsulfate, 50% glycerol and 0.02% Bromophenol Blue.

The above reaction solution (20 µl) was applied to a 1% agarose gel prepared from agarose L03 (manufactured by Takara Shuzo) and TAE buffer [consisting of 40 mM of Tris, 5 mM of sodium acetate and 1 mM of disodium ethylenediaminetetraacetate (EDTA); adjusted to pH 7.8 with acetic acid] and an electrophoresis was carried out in a TAE buffer. After the electrophoresis, the gel was dipped in a 1 µg/ml aqueous solution of ethidium bromide and irradiated with ultraviolet ray and the electrophoretic pattern of DNA was observed. Incidentally, in the control where water was added, DNA completely changed from a supercoiled type to a relaxed circular type while, when topoisomerase II activity was inhibited, the change of from the supercoiled type to the relaxed circular type was partially or completely inhibited.

As a result, in the control to which water was added, DNA was completely changed from a supercoiled type to a relaxed circular type but the change from a supercoiled type to a relaxed circular type was partially or completely inhibited by 100 μM or more of 4,5-dihydroxy-2-pentenal or 4-hydroxy-2-cyclopenten-1-one whereby the topoisomerase II-inhibiting activity of each of the compounds was confirmed.

(2) Topoisomerase I-inhibiting activity of each compound was measured by the same method as in Example 13-(1) except that topoisomerase I [manufactured by Topogen; 0.01 unit/μl] was used instead of topoisomerase II and, as a 10-fold diluted buffer, 100 mM Tris-HCl (pH 7.9), 10 mM EDTA-disodium, 1 mM spermidine and 50% glycerol were used.

The result was that no topoisomerase I-inhibiting activity was confirmed in any of the compounds.

As mentioned above, each compound showed a specific inhibiting activity to topoisomerase II which transiently appeared only in a stage of division in normal cells but is highly expressed throughout all cell periods as a result of canceration. Incidentally, all other compounds of the present invention showed the same inhibiting activity as well.

Example 14

Hs 68 cells (ATCC CRL-1635) which were human cancer cells were incubated on a D-MEM medium (manufactured by Gibco BRL) containing 10% of fetal bovine serum (FBS manufactured by BioWhittaker) at 37° C. in the presence of 5% of $CO_2$ until the cells were saturated in the culture medium, a trypsin-EDTA solution (manufactured by BioWhittaker) was suspended in the above medium to make $3\times10^5$ cells/ml and each 200 μl of the suspension were placed in each well of a 96-well microtiter plate. After five days from the incubation, the medium was discarded at the stage where the cells were almost saturated in the culture medium and a medium containing 5, 10, 20, 40, 100 or 200 μM of 4,5-dihydroxy-2-pentenal or 4-hydroxy-2-cyclopenten-1-one was added thereto. A time course of 96 hours was adopted and, every 24 hours, the supernatant liquid of the incubated medium was recovered and the influence of 4,5-dihydroxy-2-pentenal and 4-hydroxy-2-cyclopenten-1-one on the induction of hIGF-1 production in Hs68 cells was measured using an ELISA-kit for hIGF-1 (manufactured by Diagnostic System Labo).

The result was that, in Hs68 cells, the inducing activity of the hIGF production became maximum after 24 hours and then reduced with a lapse of time when 100 μM or more 4,5-dihydroxy-2-pentenal or 4-hydroxy-2-cyclopenten-1-one were added. Incidentally, the hIGF-1 inducing activity of 4-hydroxy-2-cyclopenten-1-one was stronger than that of 4,5-dihydroxy-2-pentenal.

The results are given in Table 2 and Table 3.

TABLE 2

| 4-hydroxy-2-cyclopenten-1-one Concentration (μM) | Incubation Time | | | |
|---|---|---|---|---|
| | 24 hours | 48 hours | 72 hours | 96 hours |
| | Inducing Activity of the hIGF-1 Production (ng/ml) | | | |
| 0 | 0 | 0 | 0 | 0 |
| 40 | 0 | 0 | 0 | 0 |

TABLE 2-continued

| 4-hydroxy-2-cyclopenten-1-one Concentration (μM) | Incubation Time | | | |
|---|---|---|---|---|
| | 24 hours | 48 hours | 72 hours | 96 hours |
| | Inducing Activity of the hIGF-1 Production (ng/ml) | | | |
| 100 | 39.9 | 10.0 | 9.6 | 4.4 |
| 200 | 37.9 | 10.4 | 9.9 | 4.2 |

TABLE 3

| 4,5-hydroxy-2-pentenal Concentration (μM) | Incubation Time | | | |
|---|---|---|---|---|
| | 24 hours | 48 hours | 72 hours | 96 hours |
| | Inducing Activity of the hIGF-1 Production (ng/ml) | | | |
| 0 | 0 | 0 | 0 | 0 |
| 40 | 0 | 0 | 0 | 0 |
| 100 | 15.3 | 10.0 | 5.2 | 4.6 |
| 200 | 11.3 | 11.1 | 9.9 | 4.5 |

As such, 4,5-dihydroxy-2-pentenal and 4-hydroxy-2-cyclopenten-1-one showed an inducing activity of the hIGF-1 production. Other compounds of the present invention showed the same activity as well.

Example 15

(1) U937 cells (ATCC CRL-1593) which were synovial cell strains established from pleural effusion of patients suffering from tissue lymphoma were suspended in an RPMI 1640 medium containing 10% of FBS to make its concentration $5\times10^5$ cells/ml and each 100 μl of the suspension was placed in each well of a 96-well microtiter plate. After that, 100 μl of the above medium were added and then 4,5-dihydroxy-2-pentenal or 4-hydroy-2-cyclopenten-1-one was added to make its concentration 5, 75, 100, 150 or 200 μM. The mixture was incubated at 37° C. in the presence of carbon dioxide gas and, after 24, 48 and 72 hours, 10 μl of Premix WST-1 (MK 400; manufactured by Takara Shuzo) were added. The mixture was made to react at 37° C. for three hours and the value ($A_{450-650}$) obtained by subtracting the absorbance at 650 nm ($A_{650}$) from that at 450 nm ($A_{450}$) was defined as a degree of cell growth.

The results are given in Table 4 and Table 5.

TABLE 4

| 4-hydroxy-2-cyclopenten-1-one Concentration (μM) | Incubation Time | | |
|---|---|---|---|
| | 24 hours | 48 hours | 72 hours |
| | Degree of Cell Growth ($A_{450-650}$) | | |
| 0 | 0.940 | 3.912 | 1.829 |
| 50 | 0.501 | 0.930 | 0.875 |
| 75 | 0.557 | 0.968 | 0.821 |
| 100 | 0.591 | 1.054 | 0.532 |
| 150 | 0.524 | 1.126 | 0.478 |
| 200 | 0.353 | 0.643 | 0.338 |

TABLE 5

| 4,5-dihydroxy-2-pentenal Concentration ($\mu$M) | Incubation Time | | |
|---|---|---|---|
| | 24 hours | 48 hours | 72 hours |
| | Degree of Cell Growth ($A_{450-650}$) | | |
| 0 | 0.940 | 3.912 | 1.829 |
| 50 | 0.821 | 1.471 | 1.245 |
| 75 | 0.606 | 0.879 | 0.862 |
| 100 | 0.560 | 0.948 | 0.597 |
| 150 | 0.505 | 0.823 | 0.465 |
| 200 | 0.370 | 0.644 | 0.753 |

As such, 4,5-dihydroxy-2-pentenal and 4-hydroxy-2-cyclopenten-1-one showed a cell growth suppressing activity to synovial cells. Other compounds of the present invention showed the same activity as well.

(2) DSEK cells (owned by Department of Second Internal Medicine, Total Medical Center, Saitama Medical College, as a rhematism model in vitro) which were fibroblast cell strains established from synovial membrane from a patient suffering from human chronic rheumatism were incubated in an Iscov-MEM medium (IMDM; manufactured by Gibco BRL) containing 10% of FBS (manufactured by BioWhittaker) at 37° C. in the presence of 5% $CO_2$ until the cells saturated in a incubator, a trypsin-EDTA solution (manufactured by BioWhittaker) was suspended in the above medium to an extent of $3\times10^4$ cells/ml and each 200 $\mu$l of the suspension was placed in each well of a 96-well microtiter plate (manufactured by Falcon). When the cells were almost in a state of 80% saturation after 5–7 days from incubation, the medium was exchanged and 200 $\mu$l of the above medium containing 50, 75, 100 or 150 $\mu$M of 4-hydroxy-2-cyclopenten-1-one or 4,5-dihydroxy-2-pentenal were added thereto.

A time course of 96 hours was adopted and, every 24 hours, 10 $\mu$l of Premix WST-1 (MK 400; manufactured by Takara Shuzo) were added followed by reacting at 37° C. for 3.5 hours and the value ($A_{450-650}$) obtained by subtracting the absorbance at 650 nm ($A_{650}$) from that at 450 nm ($A_{450}$) was defined as a degree of cell growth.

The results are given in Table 6 and Table 7.

Further, 50% cell growth inhibiting concentrations (-$IC_{50}$) calculated from the data of $A_{450-650}$ are shown in Table 8.

TABLE 6

| 4-hydroxy-2-cyclopenten-1-one Concentration ($\mu$M) | Incubation Time | | | |
|---|---|---|---|---|
| | 24 hours | 48 hours | 72 hours | 96 hours |
| | Degree of Cell Growth ($A_{450-650}$) | | | |
| 0 | 1.04 | 1.25 | 1.46 | 2.35 |
| 50 | 0.57 | 0.71 | 0.73 | 0.54 |
| 75 | 0.51 | 0.68 | 0.68 | 0.55 |
| 100 | 0.50 | 0.64 | 0.67 | 0.51 |
| 150 | 0.46 | 0.55 | 0.63 | 0.50 |

TABLE 7

| 4,5-dihydroxy-2-pentenal Concentration ($\mu$M) | Incubation Time | | | |
|---|---|---|---|---|
| | 24 hours | 48 hours | 72 hours | 96 hours |
| | Degree of Cell Growth ($A_{450-650}$) | | | |
| 0 | 1.04 | 1.25 | 1.46 | 2.33 |
| 50 | 1.12 | 0.83 | 0.96 | 0.98 |
| 75 | 1.11 | 0.77 | 0.67 | 0.59 |
| 100 | 1.02 | 0.63 | 0.54 | 0.59 |
| 150 | 0.96 | 0.61 | 0.41 | 0.55 |

TABLE 8

| $IC_{50}$ | 4-hydroxy-2-cyclopenten-1-one | | 4,5-dihydroxy-2-pentenal | |
|---|---|---|---|---|
| | 48 hours | 96 hours | 48 hours | 96 hours |
| Concentration ($\mu$M) | 60 | 35 | 165 | 75 |

(3) DSEK cells were prepared under the conditions as mentioned in Example 15-(2) and 20 $\mu$l of medium containing 25, 50, 75, 100, 200 or 400 $\mu$M of 4,5-dihydroxy-2-pentenal, 4-hydroxy-2-cyclopenten-1-one, 4-(9-guaninyl)-2-cyclopenten1-one or 2-(3,4-dihydroxy-1-butenyl)-4-(2-formylvinyl)-1,3-dioxolane were added thereto.

A time course of 72 hours was adopted and, every 24 hours, degree of cell growth was measured with a lapse of time. $IC_{50}$ of each of the compounds was measured as well.

The result is given in Table 9.

TABLE 9

| Name of Substance | $IC_{50}$ ($\mu$M) | |
|---|---|---|
| | 24 hours | 72 hours |
| 4-hydroxy-2-cyclopenten-1-one | 207 | 60 |
| 4,5-dihydroxy-2-pentenal | 232 | 119 |
| 4-(9-guaninyl)-2-cyclopenten-1-one | 132 | 67 |
| 2-(trans-3,4-dihydroxy-1-butenyl)-4-(trans-2-formylvinyl)-1,3-dioxolane | 267 | 68 |

Degrees of cell growth after 24 and 72 hours of the control to which no sample was added were 3.95 and 3.97, respectively.

As such, when 4,5-dihydroxy-2-pentenal, 4-hydroxy-2-cyclopenten-1-one, 4-(9-guaninyl)-2-cyclopenten1-1-one or 2-(3,4-dihydroxy-1-butenyl)-4-(2-formylvinyl)-1,3-dioxolane was added to DSEK cells (rheumatism model) in vitro, the cases where each of the compounds was added showed a significant inhibition of growth of rheumatism cells as compared with the case where PBS was added. Further, in observations with a lapse of time, it was noted that those compounds not only maintained their growth-inhibiting activity but also tended to potentiate the activity with a lapse of time.

From the above results, 4,5-dihydroxy-2-pentenal, 4-hydroxy-2-cyclopenten-1-one, 4-(9-guaninyl)-2-cyclopenten1-one and 2-(3,4-dihydroxy-1-butenyl)-4-(2-formylvinyl)-1,3-dioxolane were found to have strong antirheumatic activity and are expected to be developed as therapeutic agents and health foods useful for chronic rheumatism. Further, all other compounds of the present invention also showed the same antirheumatic activity.

Now, in the DSEK cell incubation, 150 $\mu$l/well of the supernatant liquid of the medium were recovered every 24 hours and influence of 4-hydroxy-2-cyclopenten-1-one or 4,5-dihydroxy-2-pentenal on the production of cytokines (human TGF-β, human FGF-β, human IL-1α and human IL-10) was measured using an ELISA-kit specific to each of the cytokine (the kit manufactured by INTERGEN or human FGF-β and human IL-10; and the kit manufactured by Promega for human IL-1α and human TGF-β).

The result was as follows. 4-Hydroxy-2-cyclopenten-1-one inhibited the production of human FGF-β and human IL-1α; 4-(9-guaninyl)-2-cyclopenten-1-one inhibited the production of human TGF-β and human FGF-β and activated the production of human IL-1α; 2-(3,4-dihydroxy-1-butenyl)-4-(2-formylvinyl)-1,3-dioxalane activated the production of human IL-1α; and 4,5-dihydroxy-2-pentenal activated the production of human IL-1α and human IL-10.

Example 16

HepG2 cells (ACTT HB-8065) which were the cell strains established from the patients suffering from primary hepatoblastoma were suspended in a DMEM medium (manufactured by Gibco) containing 10% of FBS (manufactured by BioWhittaker) to an extent of $3.8 \times 10^3$ cells/ml, each 200 μl of the suspension were placed in each well of a 96-well microtiter plate and incubated at 37° C. in the presence of 5% carbon dioxide gas until the cells saturated in an incubator, the medium was exchanged, then 4-hydroxy-2-cyclopenten-1-one or 4,5-dihydroxy-2-pentenal was added thereto as to be contained in an amount of 25, 50, 100 or 250 μM, the mixture was incubated for 24, 48 or 72 hours, 10 μl of Premix WST-1 (MK 400; manufactured by Takara Shuzo) were added thereto, the mixture was made to react at 37° C. for three hours and the value ($A_{450-650}$) obtained by subtracting the absorbance at 650 nm ($A_{650}$) from that at 450 nm ($A_{450}$) was defined as a degree of cell growth.

The results are given in Table 10 and Table 11.

TABLE 10

| 4-hydroxy-2-cyclopenten-1-one Concentration (μM) | Incubation Time | | |
|---|---|---|---|
| | 24 hours | 48 hours | 72 hours |
| | Degree of Cell Growth ($A_{450-650}$) | | |
| 0 | 3.47 | 2.96 | 2.57 |
| 25 | 1.30 | 0.70 | 0.49 |
| 50 | 1.38 | 0.81 | 0.47 |
| 100 | 1.31 | 0.56 | 0.35 |
| 150 | 1.23 | 0.43 | 0.30 |

TABLE 11

| 4,5-dihydroxy-2-pentenal Concentration (μM) | Incubation Time | | |
|---|---|---|---|
| | 24 hours | 48 hours | 72 hours |
| | Degree of Cell Growth ($A_{450-650}$) | | |
| 0 | 3.47 | 2.96 | 2.57 |
| 25 | 3.39 | 2.69 | 1.70 |
| 50 | 1.97 | 2.96 | 1.70 |
| 100 | 1.81 | 2.70 | 0.89 |
| 150 | 1.40 | 0.79 | 0.35 |

As such, 4-hydroxy-2-cyclopenten-1-one and 4,5-dihydroxy-2-pentenal showed an activity for suppressing the growth of cancer cells to hepatoblastoma HepG2 cells. Other compounds of the present invention showed the same activity as well.

Example 17

(1) RAW 264.7 cells (ATCC TIB 71) were suspended to an extent of $3 \times 10^5$ cells/ml in an Eagle's medium modified by Dulbecco (manufactured by BioWhittaker; 12-917F) containing 10% fetal bovine serum (manufactured by Gibco), no Phenol Red and 2 mM of L-glutamine (manufactured by Lifetech Oriental; 25030-149) and each 500 μl of the suspension were added to each well of a 48-well microtiter plate and incubated at 37° C. for 12 hours in the presence of 5% carbon dioxide gas. To the well were added 10 μl of a 50 μg/ml lipopolysaccharide (LPS; manufactured by Sigma, L-2012) or each 10 μl of a 2.5 μg/ml of LPS and a 500 units/ml of interferon γ (manufactured by Genzyme; code MG-IFN), then 10 μl of a 1000, 500 or 250 μM aqueous solution of 2-(trans-3,4-dihydroxy-1-butenyl)-4-(trans-2-formylvinyl)-1,3-dioxolane were added, the mixture was incubated for 18 hours more and the $NO_2^-$ concentration generated by oxidation of NO in the medium was measured. Incidentally, a section to which LPS and interferon γ were not added and a section to which 2-(trans-3,4-dihydroxy-1-butenyl)-4-(trans-2-formylvinyl)-1,3-dioxolane was not added were prepared as controls.

After the above incubation, 100 μl of a 4% Griess reagent (manufactured by Sigma; G4410) were added to 100 μl of the medium, the mixture was allowed to stand at room temperature for 15 minutes and the absorbance at 490 nm was measured. From a calibration curve prepared by $NaNO_2$ of known concentrations dissolved in the above medium, the $NO_2^-$ concentration in the medium was calculated. All measurements were conducted in three series.

The result was that 2-(trans-3,4-dihydroxy-1-butenyl)-4-(trans-2-formylvinyl)-1,3-dioxolane inhibited the induction of NO production by LPS and inhibited the induction of NO production by LPS and interferon γ in a concentration-dependent manner.

Figure 14:
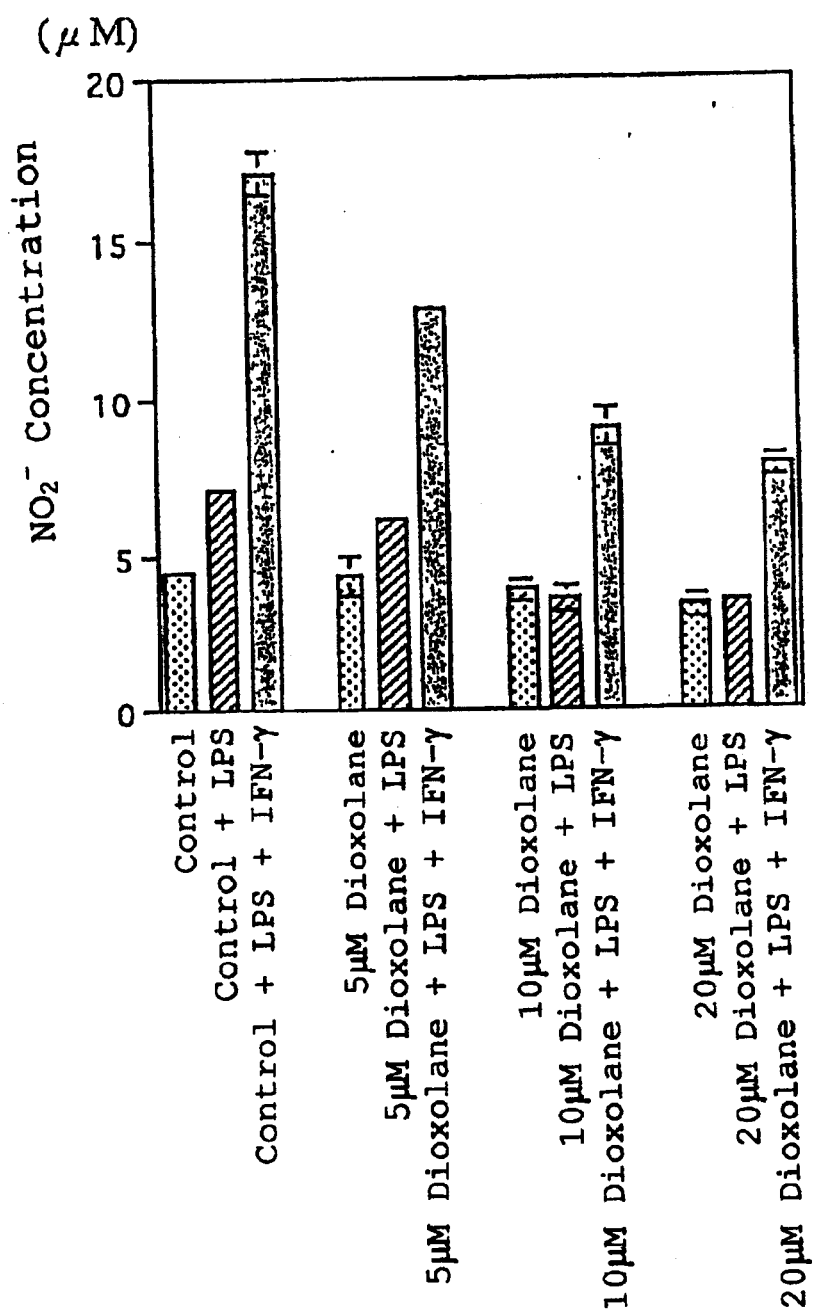
FIG. 14 shows the $NO_2^-$ concentration in the medium when 2-(trans-3,4-dihydroxy-1-butenyl)-4-(trans-2-formylvinyl)-1,3-dioxolane was added followed by incubating under each of the incubating conditions.

The result is given in FIG. 14. Thus, FIG. 14 shows the $N_2^-$ concentration in the medium when 2-(trans-3,4-dihydroxy-1-butenyl)-4-(trans-2-formylvinyl)-1,3-dioxolane was added followed by incubating under each of the incubating conditions. In FIG. 14, an abscissa indicates incubating conditions and an ordinate indicates $NO_2^-$ concentrations (μM). In the drawing, 2-(trans-3,4-dihydroxy-1-butenyl)-4-(trans-2-formylvinyl)-1,3-dioxolane was referred to just "dioxolane".

Even at the final concentration of 10 μM where no inhibition of cell growth was noted at all, 2-(trans-3,4-dihydroxy-1-butenyl)-4-(trans-2-formylvinyl)-1,3-dioxolane showed an inhibiting activity for NO production to an extent of about 50%. This result indicates that the inhibition of NO production by 2-(trans-3,4-dihydroxy-1-butenyl)-4-(trans-2-formylvinyl)-1,3-dioxolane is not caused by inhibition of cell growth by 2-(trans-3,4-dihydroxy-1-butenyl)-4-(trans-2-formylvinyl)-1,3-dioxolane. All other compounds of the present invention showed the same activity as well.

Example 18

Each 5 ml of an RPMI 1640 medium containing 10% of FBS containing $2 \times 10^5$ cells/ml of HL-60 (ATCC CCL-240) were placed in each well of a six-well plate, incubated at 37° C. for 24 hours in the presence of 5% $CO_2$, then 4,5-dihydroxy-2-pentenal was added to make the final concentration 0, 12.5, 25, 50 or 100 μM or 4-hydroxy-2-cyclopenten-1-one was added to make the final concentration 0, 2.5, 5, 10, 20, 40 or 80 μM and the mixture was incubated for six hours more.

After completion of the incubation, cell numbers were counted and then the cells were recovered by centrifugation and washed with PBS to prepare the cells treated with each of the samples. In addition, cells which were heated at 45° C. for five minutes followed by subjecting to the same incubation were prepared as well.

The cells treated as such were then subjected to an SDS-PAGE according to a method mentioned in "Molecular Cloning" (Cold Spring Harbor Laboratory Press, 1989). Thus, the cells were suspended in an SDS-PAGE sample buffer to make the concentration $2.5 \times 10^6$ cells/ml, the resulting cell suspension was treated at 100° C. for ten minutes, each 5 µl thereof were applied to two sheets of SDS-PAGE gel (a 5% stacking gel and a 10% separation gel) and an electrophoresis was carried out. One of the gels was stained with Coomassie while another was subjected to a blotting to polyvinylidene difluoride transfer membrane (Immobilon™ manufactured by MILLIPORE; catalog no. IPVH000-10). This membrane was subjected to a blocking overnight at 4° C. using Block Ace (manufactured by Dainippon Pharmaceutical; catalog no. UK-B25).

The membrane which was subjected to a blocking as such was made to react with monoclonal antibody HSP 72/73 (Ab-1) (manufactured by Oncogene Research Products; catalog no. HSP01) which specifically reacted with heat-induced heat shock protein of 70 kDa, washed with TBS containing 0.05% Tween 20 and further washed with TBS. After that, it was made to react with peroxidase-compounded secondary antibody HRP-Rabbit Anti Mouse IgG (H+L) (manufactured by ZYMED Laboratories; catalog no. 61-6520) and washed as same as in the previous operation. The membrane which was made to react with the primary antibody and the secondary antibody as such was made to react with RENAISSANCE™ (a chemiluminol reagent manufactured by Dupont NEN, catalog no. NEL-100) and then exposed to X-ray film to confirm the induction of the heat shock protein of 70 kDa.

As a result, induction of heat shock protein by 4,5-dihydroxy-2-pentenal and by 4-hydroxy-2-cyclopenten-1-one was confirmed. Degree of intensity of the induction was shown in Table 12 and Table 13. In Tables 12 and 13, "+" shows the intensity of induction and the more the "+", the more the induction. Incidentally, "−" means no induction and "±" means a little induction. All other compounds of the present invention showed the same heat shock protein inducing activity as well.

TABLE 12

| | Concentration (µM) | | | |
|---|---|---|---|---|
| | 1.25 | 25 | 50 | 100 |
| 4,5-dihydroxy-2-pentenal | − | ± | +++ | − |

TABLE 13

| | Concentration (µM) | | | | | |
|---|---|---|---|---|---|---|
| | 2.5 | 5 | 10 | 20 | 40 | 80 |
| 4-hydroxy-2-cyclopenten-1-one | − | ± | + | +++ | ++ | ± |

Incidentally, untreated cell suspension showed "−" (no induction) and cell suspension which was heated at 45° C. for 5 minutes showed "++".

Example 19

Injection

The neutralization product of the heat-treated D-ribose which is described in Example 1 was concentrated and dried. Then the resulting product was dissolved in distilled water for injection to prepare 1% solution. This solution was packed in vials for freeze-drying in an amount of 10 mg based upon the supernatant fraction and then freeze-dried. A physiological saline solution (2 ml) was separately attached thereto as a solvent for dissolution.

By the same manner, the heat-treated 2-deoxy-D-ribose which is described in Example 2 was used to prepare injection.

By the same manner, 4,5-dihydroxy-2-pentenal, 4-hydroxy-2-cyclopenten-1-one, 4-(9-adeninyl)-2-cyclopenten-1-one, 4-(9-guaninyl)-2-cyclopenten-1-one, 2-(3,4-dihydroxy-1-butenyl)-4-(2-formylvinyl)-1,3-dioxolane1 or 5-epoxy-1-hydroxy-3-penten-2-one was used to prepare injection.

Example 35

Tablets

Tablets were prepared in accordance with the following formulation.

| | |
|---|---|
| Heat-treated sodium salt of DNA | 10 mg |
| Corn starch | 65 mg |
| Carboxymethylcellulose | 20 mg |
| Polyvinylpyrrolidone | 3 mg |
| Magnesium stearate | 2 mg |
| Total | 100 mg per tablet |

The freeze-dried product of heat-treated sodium salt of DNA which is described in Example 4 was used.

By the same manner, 4,5-dihydroxy-2-pentenal, 4-hydroxy-2-cyclopenten-1-one, 4-(9-adeninyl)-2-cyclopenten-1-one, 4-(9-guaninyl)-2-cyclopenten-1-one, 2-(3,4-dihydroxy-1-butenyl)-4-(2-formylvinyl)-1,3-dioxolane1 or 5-epoxy-1-hydroxy-3-penten-2-one was used to prepare tablets.

MERIT OF THE INVENTION

The present invention offers the heat-treated product of the present invention and/or a partially purified product thereof having an apoptosis-inducing ability which induces apoptosis to cancer cells in cancer and is effective for the prevention and treatment of cancer, and also offers the compound of the present invention which is a substance having an apoptosis-inducing ability. The present invention also offers a method for the manufacture of 4-hydroxy-2-cyclopenten-1-one from pentose other than uronic acid group. Indigestive cancers such as colonic cancer and gastric cancer, in particular, the apoptosis of the cancer cells can be induced by orally taking a compound which is selected from the heat-treated product of the present invention and/or a partially purified product thereof or the compound having an apoptosis-inducing ability as food or beverage. Thus food or beverage which a compound selected from the heat-treated product of the present invention and/or a partially purified product thereof or the compound having an apoptosis-inducing ability contained therein, added thereto and/or diluted therewith is quite effective for the prevention and treatment of digestive cancers. The pharmaceutical agents which contain a compound which is selected from the heat-treated product of the present invention and/or a partially purified product thereof or the compound having an apoptosis-inducing ability as an effective component has a cell growth suppressing activity to cancer cells and growth of abnormal cells of synovial cells, and are highly effective for maintaining the homeostasis of living body. Due to a hIGF production inducing ability, said pharmaceutical agents are also effective for the treatment and prevention of disease requiring the induction of hIGF-1 production. Said pharmaceutical agents are also effective for the treatment and prevention of disease requiring the suppression of active oxygen, for example the suppression of NO production. Furthermore, due to heat shock protein inducing ability, said pharmaceutical agents are effective for the treatment and prevention of disease requiring the induction of heat shock protein, for example viral disease.

It is possible to supply the heat-treated product of the present invention and/or a partially purified product thereof or the compound having an apoptosis-inducing ability at a low price in a large amount from using foods as material. Furthermore, the present invention offers a method for conveniently inducing apoptosis by using the heat-treated product of the present invention and/or a partially purified product thereof or the compound having an apoptosis-inducing ability as an effective component whereupon the study of mechanism of apoptosis and the development of apoptosis-inducing inhibitor can be conducted by using said method.

Furthermore, the present invention offers the pharmaceutical agents which use a compound selected from the compound of the present invention. Said pharmaceutical agents are highly effective for the treatment and prevention of intractable diseases such as cancer, rheumatics, diabetes mellitus and viral disease.

The present invention further offers food or beverage which a compound selected from the compound of the present invention contained therein, added thereto and/or diluted therewith. Said food or beverage is a functional food or beverage such as apoptosis-inducing, carcinostatic, antirheumatic, anti-diabetes mellitus and heat shock protein inducing food or beverage which is effective for the prevention and improvement of intractable diseases such as cancer, rheumatics, diabetes mellitus and viral disease.

The present invention further offers a convenient method for the manufacture of 4,5-dihydroxy-2-pentenal and 4-hydroxy-2-cyclopenten-1-one. Furthermore, the present invention offers the novel compound having physiological activity such as 4-(9-adeninyl)-2-cyclopenten-1-one, 4-(9-guaninyl)-2-cyclopenten-1-one, 2-(3,4-dihydroxy-1-butenyl)-4-(2-formylvinyl)-1,3-dioxolane1, 5-epoxy-1-hydroxy-3-penten-2-one and the compound represented by the formula [I].

What is claimed is:
1. A pharmaceutical agent for therapy of rheumatism, characterized in that said pharmaceutical agent contains a compound selected from 2-(3,4-dihydroxy-1-butenyl)-4-(2-formylvinyl)-1,3-dioxolane, and 4(9-guaninyl)-2-cyclopenten-1-one as the effective component.
2. A compound selected from
4-(9-adeninyl)-2-cyclopenten-1-one,
4-(9-guaninyl)-2-cyclopenten-1-one,
1,5-epoxy-1-hydroxy-3-penten-2-one,
2-(3,4-dihydroxy-1-butenyl)-4-(2-formylvinyl)-1,3-dioxolane, and
the compound represented by the following formula [II]

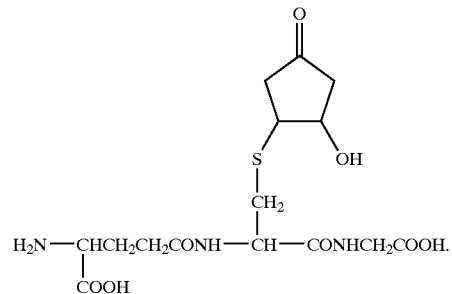

3. A pharmaceutical agent characterized in that said pharmaceutical agent contains a compound selected from
4-(9-adeninyl)-2-cyclopenten-1-one,
4-(9-guaninyl)-2-cyclopenten-1-one,
2-(3,4-dihydroxy-1-butenyl)-4-(2-formylvinyl)-1,3-dioxolane,
1,5-epoxy-1-hydroxy-3-penten-2-one, and
the compound represented by the formula [II] as an effective component

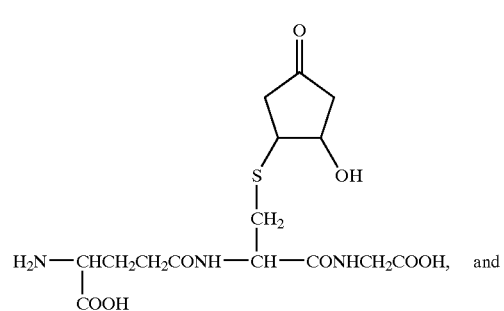

a pharmaceutical carrier.

* * * * *